(12) United States Patent
Sharma et al.

(10) Patent No.: US 7,326,707 B2
(45) Date of Patent: Feb. 5, 2008

(54) BICYCLIC MELANOCORTIN-SPECIFIC COMPOUNDS

(75) Inventors: Shubh D. Sharma, Cranbury, NJ (US); Yi-Qun Shi, East Brunswick, NJ (US); Zhijun Wu, Plainsboro, NJ (US); Ramesh Rajpurohit, Hillsboro, NJ (US)

(73) Assignee: Palatin Technologies Incorporated, Cranbury, NJ (US)

( * ) Notice: Subject to any disclaimer, the term of this patent is extended or adjusted under 35 U.S.C. 154(b) by 436 days.

(21) Appl. No.: 10/761,889

(22) Filed: Jan. 21, 2004

(65) Prior Publication Data

US 2004/0152134 A1    Aug. 5, 2004

Related U.S. Application Data

(63) Continuation-in-part of application No. PCT/US02/25574, filed on Aug. 12, 2002.

(60) Provisional application No. 60/441,139, filed on Jan. 17, 2003, provisional application No. 60/311,404, filed on Aug. 10, 2001.

(51) Int. Cl.
  *A01N 43/60* (2006.01)
  *C07D 241/36* (2006.01)
  *C07D 241/38* (2006.01)
(52) U.S. Cl. .................. 514/249; 544/338
(58) Field of Classification Search .......... 514/249; 544/338
  See application file for complete search history.

(56) References Cited

U.S. PATENT DOCUMENTS

| | | | |
|---|---|---|---|
| 4,148,923 A | 4/1979 | Giudicelli et al. |
| 4,239,763 A | 12/1980 | Milavec et al. |
| 4,626,549 A | 12/1986 | Molloy et al. |
| 4,680,289 A | 7/1987 | Applezweig |
| 4,937,267 A | 6/1990 | Holloway et al. |
| 5,120,713 A | 6/1992 | Mugica |
| 5,639,778 A | 6/1997 | Andersson et al. |
| 5,804,578 A | 9/1998 | Chakravarty et al. |
| 5,877,182 A | 3/1999 | Nargund et al. |
| 5,880,125 A | 3/1999 | Nargund et al. |
| 5,965,565 A | 10/1999 | Chen et al. |
| 6,033,656 A | 3/2000 | Mikami et al. |
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,699 B1 | 3/2001 | Rothman |
| 6,214,831 B1 | 4/2001 | Yokoo et al. |
| 6,284,735 B1 | 9/2001 | Girten et al. |
| 6,350,760 B1 | 2/2002 | Bakshi et al. |
| 6,376,509 B1 | 4/2002 | Bakshi et al. |
| 6,410,548 B2 | 6/2002 | Nargund et al. |
| 6,451,783 B1 | 9/2002 | Hadcock et al. |
| 6,458,790 B2 | 10/2002 | Palucki et al. |
| 6,472,398 B1 | 10/2002 | Palucki et al. |
| 6,515,122 B1 | 2/2003 | Lang et al. |
| 6,534,503 B1 | 3/2003 | Dines et al. |
| 6,579,968 B1 | 6/2003 | Blood et al. |
| 2002/0004512 A1 | 1/2002 | Bakshi et al. |
| 2002/0019523 A1 | 2/2002 | Palucki et al. |
| 2002/0072604 A1 | 6/2002 | Carpino et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2003/0004162 A1 | 1/2003 | Treadway |
| 2003/0069169 A1 | 4/2003 | Macor et al. |
| 2003/0083228 A1 | 5/2003 | Carpino et al. |
| 2003/0092732 A1 | 5/2003 | Yu et al. |
| 2003/0109556 A1 | 6/2003 | Mazur et al. |
| 2003/0195212 A1 | 10/2003 | Lundstedt et al. |
| 2004/0024211 A1 | 2/2004 | Boyce et al. |

FOREIGN PATENT DOCUMENTS

WO   WO 98/10653   3/1998
WO   WO 99/55679   11/1999

(Continued)

OTHER PUBLICATIONS

Cornille et al., Tetrahedron Letters, vol. 35, No. 38, pp. 6989-6992, 1994.*

(Continued)

*Primary Examiner*—Mark L. Shibuya
(74) *Attorney, Agent, or Firm*—Morgan Lewis & Bockius LLP

(57) ABSTRACT

Melanocortin receptor-specific bicyclic compounds having the structure:

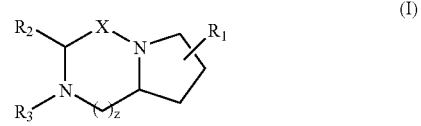

(I)

and stereoisomer and pharmaceutically acceptable salts thereof, where $R_1$, $R_2$, $R_3$ X and z are as described in the specification, which are agonists, antagonists or mixed agonists and antagonists at one or more melanocortin receptors, and having utility in the treatment of melanocortin receptor-related disorders and conditions. Pharmaceutical compositions containing a compound of structure (I) and methods relating to the use thereof are also disclosed.

56 Claims, No Drawings

FOREIGN PATENT DOCUMENTS

| | | |
|---|---|---|
| WO | WO 99/58501 | 11/1999 |
| WO | WO 99/64002 | 12/1999 |
| WO | WO 00/05373 | 2/2000 |
| WO | WO 01/21647 | 3/2000 |
| WO | WO 00/35952 | 6/2000 |
| WO | WO 00/40247 | 7/2000 |
| WO | WO 01/05401 | 1/2001 |
| WO | WO 01/12176 | 2/2001 |
| WO | WO 01/18210 | 3/2001 |
| WO | WO 01/21634 | 3/2001 |
| WO | WO 01/23392 | 4/2001 |
| WO | WO 01/30343 | 5/2001 |
| WO | WO 01/55106 | 8/2001 |
| WO | WO 01/55107 | 8/2001 |
| WO | WO 01/55109 | 8/2001 |
| WO | WO 01/91752 | 12/2001 |
| WO | WO 02/00654 | 1/2002 |
| WO | WO 02/12178 | 2/2002 |
| WO | WO 02/18437 | 3/2002 |
| WO | WO 02/47670 | 6/2002 |
| WO | WO 02/059108 | 8/2002 |
| WO | WO 02/059117 | 8/2002 |
| WO | WO 02/064091 | 8/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 03/006620 | 1/2003 |
| WO | WO 03/066587 | 2/2003 |
| WO | WO 03/020724 | 3/2003 |
| WO | WO 03/027239 | 4/2003 |
| WO | WO 03/045920 | 6/2003 |
| WO | WO 03/055477 | 7/2003 |
| WO | WO 03/066597 | 8/2003 |
| WO | WO 03/072056 | 9/2003 |
| WO | WO 03/094918 | 11/2003 |

OTHER PUBLICATIONS

Adan, Roger A., et al., "Identification of Antagonist for Melanocortin MC3, MC4, and Mc5 Receptors", *European Journal of Pharmacology, Section 269* (1994), (1994),331-337.

Door, Robert T., et al., "Evaluation of Melanotan-II, A Superpotent Cyclic Melanotropic Peptide in a Pilot Phase Clinical Study", *Life Science*, vol. 58, No. 20, (1996), 1777-1784.

Grant, G A., "Synthetic Peptides: A Users Guide", *GA Grant, editor*, W.H. Freeman & Co., New York 1992, (1992), 11-24.

Hadley, M E., et al., "Discovery and Development of Novel Melanogenic Drugs: Melanotan-I and -II", Ronald. T. Borchardt, et al. editors; *Integration of Pharmaceutical Discovery and Development: Case Histories, Plenum Press*, New York (1998), (1998),575-595.

Hruby, V J., et al., "Emerging Approaches in the Molecular Design of Receptor-Selective Peptide Ligands: Conformational, Topographical and Dynamic Considerations", *Biochemical Journal*, (1990) 268, (1990),249-262.

Toniolo, C , "Conformationally Restricted Peptides Through Short-Range Cyclizations", *International Journal Peptide Protein Research, 35*, (1990), (1990),287-300.

\* cited by examiner

BICYCLIC MELANOCORTIN-SPECIFIC COMPOUNDS

CROSS-REFERENCE TO RELATED APPLICATIONS

This application is a continuation-in-part application of International Application No. PCT/US02/25574, International Publication No. WO 03/013571, entitled "Peptidomimetics of Biologically Active Metallopeptides", filed on Aug. 12, 2002 and the specification thereof is incorporated herein by reference.

This application claims the benefit of the filing of U.S. Provisional Patent Application Ser. No. 60/441,139, entitled "Ring Core Compounds Specific for Melanocortin Receptors", filed on Jan. 17, 2003; and of U.S. Provisional Patent Application Ser. No. 60/311,404, entitled "Receptor-Specific Peptides Derived from Biologically Active Metallopeptides", filed on Aug. 10, 2001, and the specification thereof of each is incorporated herein by reference.

BACKGROUND OF THE INVENTION

1. Field of the Invention (Technical Field)

The present invention relates to bicyclic ring core structure molecules with three or four pendant groups that bind to one or more melanocortin receptors and are agonists, antagonists or mixed agonist-antagonists.

2. Description of Related Art

Note that here and elsewhere the specification refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of tissues.

In general, compounds specific for MC1-R are believed to be useful for treatment of melanoma and melanin-associated disorders. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and other food intake and metabolism-related purposes and disorders. Compounds specific for MC3-R and MC4-R, among other melanocortin receptors, can be used as agents for treatment of sexual dysfunction, including male erectile dysfunction. Other melanocortin receptor-specific compounds, such as MCR-1 agonists, can be used as tanning agents to increase melanin production. Compounds specific for MCR-1 and MCR-3 may be useful in regulation of inflammatory processes.

WO 02/085925, "Melanocortin Receptor Ligands", to The Proctor & Gamble Company, and WO 03/094918, "Substituted Piperazines as Melanocortin Receptor Ligands", to Neurocrine Biosciences, Inc., among other applications, disclose a variety of ring core structures, but none disclose 5,5 or 6,5 ring structures, including at least two nitrogen ring atoms.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

BRIEF SUMMARY OF THE INVENTION

In one embodiment the invention provides a bicyclic core compound having the structure:

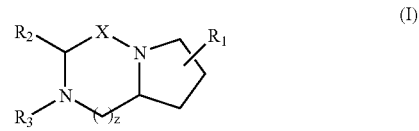

or a stereoisomer or pharmaceutically acceptable salt thereof, wherein $R_1$ is -$L_1$-J;

$R_2$ is $(CH_2)_y$—W;

$R_3$ is -$L_2$-Q;

$L_1$ is a linker selected from the group consisting of —$(CH_2)_y$—, —O—$(CH_2)_y$—, —O—, —NH—$(CH_2)_y$—, —(C=O)($CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings comprise 5 or 6 ring atoms;

W is a heteroatom unit with one cationic center, hydrogen bond donor or hydrogen bond acceptor wherein at least one atom is N;

$L_2$ is a linker selected from the group consisting of

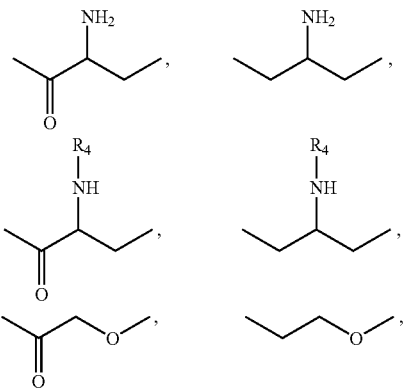

-continued

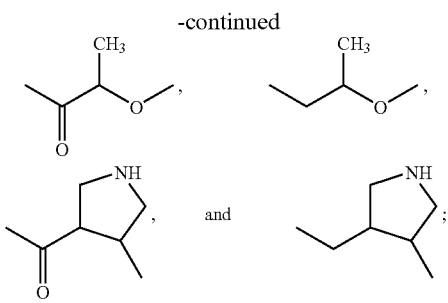

Q is an aromatic carbocyclic ring selected from the group consisting of phenyl, substituted phenyl, naphthyl and substituted naphthyl;

$R_4$ is a unit selected from the group consisting of an amine capping group, an amino acid residue, and an amino acid residue with an amine capping group;

X is $CH_2$ or C=O;

z is 0 or 1; and y is at each occurrence independently from 1 to 6.

In yet another embodiment the invention provides a bicyclic compound of the following structure:

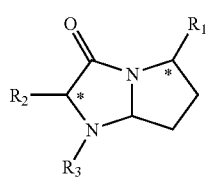

(II)

or a stereoisomer or pharmaceutically acceptable salt thereof, wherein $R_1$ is $-L_1-J$;

$R_2$ is $(CH_2)_y-W$;

$R_3$ is $-L_2-Q$;

$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings comprise 5 or 6 ring atoms;

W is a heteroatom unit with one cationic center, hydrogen bond donor or hydrogen bond acceptor wherein at least one atom is N;

$L_2$ is a linker selected from the group consisting of

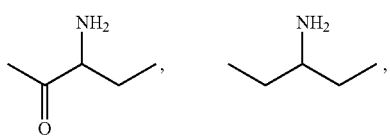

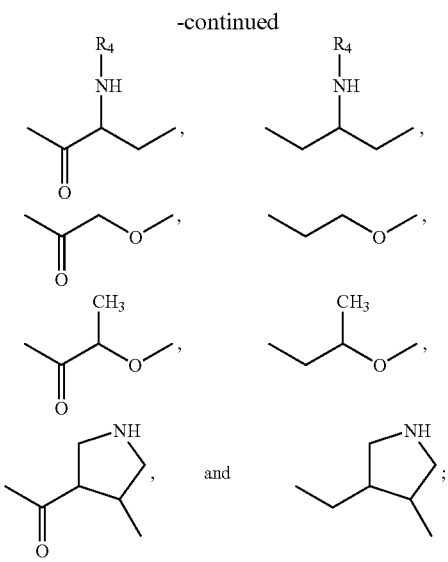

Q is an aromatic carbocyclic ring selected from the group consisting of phenyl, substituted phenyl, naphthyl and substituted naphthyl;

$R_4$ is a unit selected from the group consisting of an amine capping group, an amino acid residue, and an amino acid residue with an amine capping group; and y is at each occurrence independently from 1 to 6;

wherein the carbon atoms marked with an asterisk can have any stereochemical configuration.

In yet another embodiment the invention provides a bicyclic compound of the following structure:

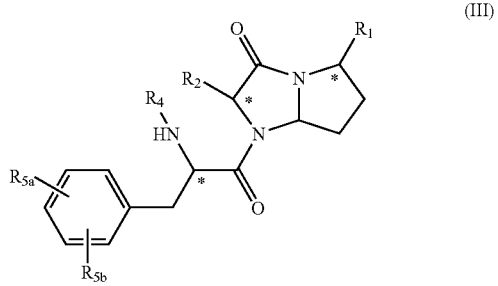

(III)

or a stereoisomer or pharmaceutically acceptable salt thereof, wherein $R_1$ is $-L_1-J$;

$R_2$ is $(CH_2)_y-W$;

$R_4$ is H or a unit selected from the group consisting of an amine capping group, a second amino acid residue, and a second amino acid residue with an amine capping group;

$R_{5a}$ and $R_{5b}$ are optional ring substituents, and when one or both are present, are the same or different and independently hydroxyl, halogen, alkyl, or aryl groups;

$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings comprise 5 or 6 ring atoms;

W is a heteroatom unit with at least one cationic center; wherein at least one atom is N; and y is at each occurrence independently from 1 to 6;

wherein the carbon atoms marked with an asterisk can have any stereochemical configuration.

In any of the foregoing, J is preferably a one of the following substituted or unsubstituted ring structures:

The J ring can be functionalized with one or more halogen, alkyl or aryl groups attached directly or through an ether linkage.

In a preferred embodiment, $R_1$ is

In an alternative preferred embodiment, $R_1$ is

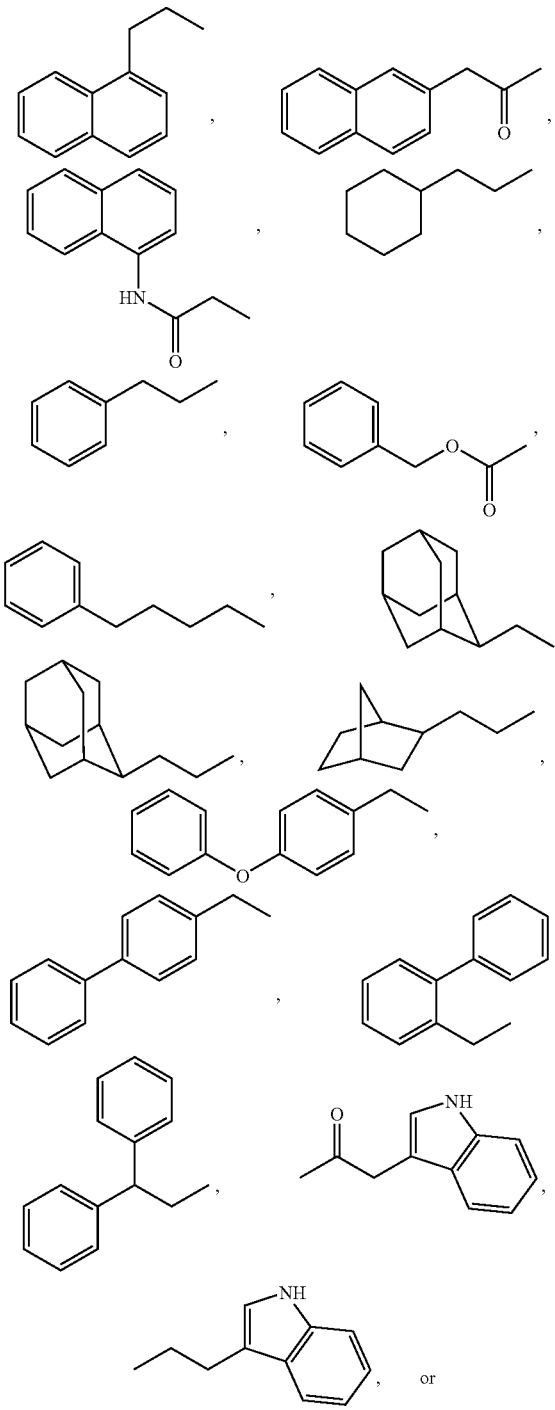

In another preferred embodiment, W is a cationic center and is $NH_2$ and $NH(C=NH)NH_2$. Alternatively, W can be —$NHCOCH_3$, —$CONHCH_3$, —$NH(C=NH)NHMe$, —$NH(C=NH)NHEt$, —$NH(C=NH)NHPr$, —$NH(C=NH)NHPr$—I, —$NH(C=NH)NH_2$,

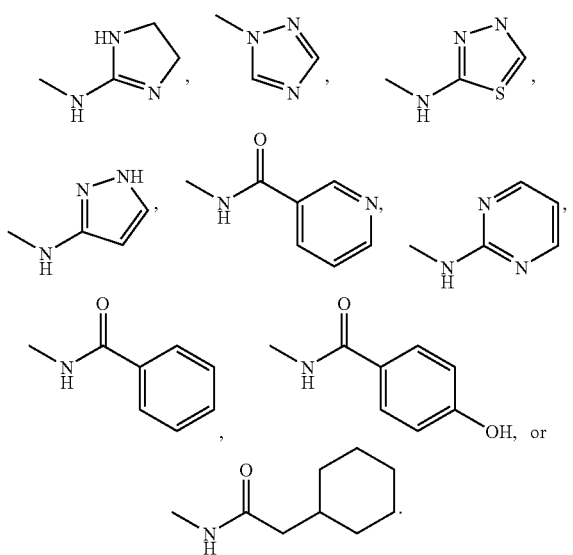

Thus $R_2$ may be

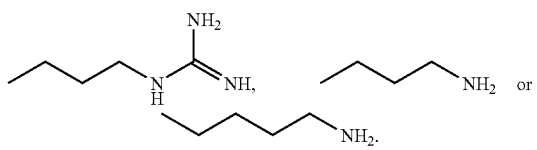

In the foregoing formulas where Q is provided, Q may be

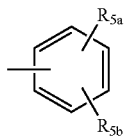

where $R_{5a}$ and $R_{5b}$ are optional ring substituents, and when one or both are present, are the same or different and independently hydroxyl, halogen, alkyl, or aryl groups attached directly or through an ether linkage. In one embodiment, the alkyl group is —$CH_3$ or —$OCH_3$.

In the foregoing formulas where $R_4$ is an amine capping group, the amino capping group may be hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc, or 8-Aoc.

In the foregoing formulas, $R_3$ may be a D-amino acid including an aromatic carbocyclic ring selected from the group consisting of phenyl, substituted phenyl, naphthyl and substituted naphthyl, or alternatively may further include an amine capping group, or in yet another $R_3$ may be dipeptide including a D-amino acid with an aromatic carbocyclic ring selected from the group consisting of phenyl, substituted phenyl, naphthyl and substituted naphthyl and a second amino acid residue, wherein the D-amino acid is bonded to the ring nitrogen. $R_3$ is a dipeptide wherein the second amino acid residue has a amine capping group. The D-amino acid may be Phe or a derivative or homolog thereof, such as for example Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe (2,4-diMe), Phe(2-Cl, 4-CF$_3$), or Phe(3,4-di-OMe). Alternatively, the D-amino acid may be Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys (Z-2'Br), Lys(Bz), Thr(Bzl), Cys(Bzl), (N-PhEt)Nal2, Phg, 3-Pya, Qal(2'), Sal, Tpi, Tyr( 2,6-DiCl-Bzl) or Tyr(Bzl). The second amino acid residue is preferably an L-amino acid, such as Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr (O-Phenyl), Thr(O-4-Cl-Phenyl) and Thr(O-2-Cl-Phenyl), Nle, Leu, Ile, Val or Beta-Ala.

In any of the forgoing, the amine capping group can be a terminal group moiety, such as hexyl, hexanoyl, heptanoyl, acetyl, phenylacetyl, cyclohexylacetyl, naphthylacetyl, cinnamoyl, benzyl, benzoyl, 7'-amino heptanoyl, 12-Ado, 6-Ahx, Amc, or 8-Aoc.

In another embodiment the present invention provides a compound that is an agonist of a melanocortin receptor, including MC1-R, MC3-R, MC4-R, or MC5-R. The compound can also be an antagonist of a melanocortin receptor, including MC1-R, MC3-R, MC4-R, or MC5-R.

The invention further comprises a method for altering a disorder or condition associated with the activity of a melanocortin receptor, comprising administering to a patient a therapeutically effective amount a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

A primary object of the present invention is to provide bicyclic core compounds, preferably 5,5 and 6,5 bicyclic compounds, specific for one or more melanocortin receptors.

Another object of the present invention is to provide bicyclic core compounds that are useful for the treatment of eating disorders such as obesity and associated impairment of energy homeostasis.

Another object of the present invention is to provide a pharmaceutical compound useful for the treatment of disorders or conditions such as anorexia and cachexia.

Yet another object of the present invention is to provide melanocortin receptor specific compounds that are useful the treatment of sexual dysfunction including erectile dysfunction and female sexual dysfunction.

A further object of the present invention is to provide compounds that are specific for at least one of melanocortin receptors MC1-R, MC3-R, MC4-R, or MC5-R and which are agonists or antagonists.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Definitions. Certain terms used in this invention, and as used in the specification and claims, are defined as follows:

The "amino acid" and "amino acids" include the known naturally occurring protein amino acids, which are referred to by both their common three letter abbreviation and single letter abbreviation. See generally *Synthetic Peptides: A User's Guide*, G A Grant, editor, W. H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, and any derivative of an amino acid side chain moiety, as the term "detivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The following abbreviations for amino acids or amino acid side chain moieties have the meanings given, it being understood that any amino acid listed may be in the L- or D-configuration:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| Aib | alpha-aminoisobutyric acid |
| Aic | 2-aminoindane-2-carboxylic acid |
| 6-Ahx | 6-amino hexanoic acid |

-continued

| | |
|---|---|
| Amb | 4-(aminomethyl)-benzoic acid |
| Amc | 4-(aminomethyl)-cyclohexane carboxylic acid |
| 7'-amino-heptanoyl | $NH_2$—$(CH_2)_6$CO— |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Beta-hHyp(Bzl) | Beta-(O-benzyl)-homohydroxyproline |
| Beta-hSer(Bzl) | Beta-(O-benzyl)-homoserine |
| Bip | biphenylalanine |
| Bzl | benzyl |
| Bz | benzoyl |
| Cha | cyclohexylalanine |
| Chg | cyclohexylglycine |
| Cmpi | 4-caboxymethyl-piperazine |
| Dip | 3,3-diphenylalanine |
| Disc | 1,3-dihydro-2H-isoindolecarboxylic acid |
| Dpr(beta-Ala) | $N^{beta}$-(3-aminopropionyl)-alpha,beta-diaminopropionic acid |
| Et- | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Heptanoyl | $CH_3$—$(CH_2)_5$CO— |
| hPhe | homophenylalanine |
| hSer | homoserine |
| Hyp | hydroxy proline |
| hHyp | homo hydroxy proline |
| Hyp(Bzl) | O-benzyl-hydroxyproline |
| Hyp(2-naphthly) | O-2'-naphthyl-hydroxyproline |
| Hyp(Phenyl) | phenyl-hydroxyproline |
| Idc | indoline-2-carboxylic acid |
| Igl | indanylglycine |
| Inp | isonipecotic acid |
| Lys(Z) | N-epsilon-benzyloxycarbonyl-lysine |
| Me- | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl—$CH_2$CO— |
| (Nlys)Gly | N-(4-aminobutyl)-glycine |
| (N-PhEt)Nal 2 | N(2-phenylethyl)-3-(2-naphthyl) alanine |
| OcHx | cyclohexyl ester |
| Phg | phenylglycine |
| pF-Phe | para-fluoro-phenylalanine |
| Phe(4-Br) | 4-bromo-phenylalanine |
| Phe(4-$CF_3$) | 4-trifluoromethyl-phenylalanine |
| Phe(4-Cl) | 4-chloro-phenylalanine |
| Phe(2-Cl) | 2-chloro-phenylalanine |
| Phe(3-Cl) | 3-chloro-phenylalanine |
| Phe(2,4-diCl) | 2,4,-dichloro-phenylalanine |
| Phe(2,4-diF) | 2,4-difluoro-phenylalanine |
| Phe(3,4-diCl) | 3,4,-dichloro-phenylalanine |
| Phe(5-Cl) | 5-chloro-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-OMe) | 4-methoxy-phenylalanine |
| Phe(4-CN) | 4-cyano-phenylalanine |
| Phe(4-$NO_2$) | 4-nitro-phenylalanine |
| Pip | pipecolic acid |
| Pr | propyl |
| Pr-I | isopropyl |
| 3-Pya | 3-pyridylalanine |
| Pyr | pyroglutamic acid |
| Qal(2') | beta-(2-quinolyl)-alanine |
| Sal | 3-styrylalanine |
| Sar | sarcosine |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |

-continued

| | |
|---|---|
| Ser(p-Cl-Bzl) | O-4-Cl-Benzyl-serine |
| Thr(Bzl) | O-Benzyl-threonine |
| Tic | 1,2,3,4-tetrahydroisoquinoline-3-carboxylic acid |
| Tiq | 1,2,3,4-tetrahydroisoquinoline-1-carboxylic acid |
| Tle | tert-butylalanine |
| Tpi | 1,2,3,4-tetrahydronorharman-3-carboxylic acid |
| Tyr(Bzl) | O-benzyl-tyrosine |
| Tyr(2,6-DiCl-Bzl) | O-(2,6 dichloro)benzyl-tyrosine |
| Z | benzyloxycarbonyl |

Conventional amino acid residues have their conventional meaning as given in Chapter 2400 of the *Manual of Patent Examining Procedure*, 7$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

The term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthyl, 1-naphthyl, and 2-naphthyl, derivatives thereof, and the like.

The term "aralkyl" includes a radical -R$^a$R$^b$ where R$^a$ is an alkylene (a bivalent alkyl) group and R$^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO-, where R is an organic group. An example is the acetyl group $CH_3CO-$.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl including groups such as hexyl, hexanoyl, heptanoyl, acetyl, phenylacetyl, cyclohexylacetyl, naphthylacetyl, benzyl, benzoyl, cinnamoyl, 7'-amino heptanoyl, 12-Ado, 7-, 6-Ahx, Amc, and 8-Aoc.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more additional pharmaceutically active ingredients or agents.

A variety of chemicals and compounds are employed in this invention, and the following abbreviations have the meanings given:

| | |
|---|---|
| Boc | tertiary butyloxycarbonyl |
| Cbz | benzyloxycarbonyl |
| DCM | dichloromethane |
| DIC | 1,3-diisopropylcarbodiimide |
| DMF | N,N-dimethylformamide |
| Fmoc | 9-fluorenylmethoxycarbonyl |
| HOAt | 1-hydroxy-7-azabenzotriazole |
| LAH | lithium aluminum hydride |
| NMM | N-methyl-morpholine |
| TBTU | 2-(1H-Benzotriazole-1-yl)-1,1,3,3-tetramethyluronium tetrafluoroborate |
| TEA | triethylamine |
| TFA | trifluoroacetic acid |
| THF | tetrahydrofuran |

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, which can interact with a melanocortin receptor and initiate a pharmacological response characteristic of the melanocortin receptor. By a melanocortin receptor "antagonist" is meant a drug or a compound, including a compound of this invention, which opposes the melanocortin receptor-associated responses normally induced by a melanocortin receptor agonist agent.

By "binding affinity" is meant the ability of a compound or drug to bind to its biological target.

In one embodiment, the invention provides a compound of the general formula (IV):

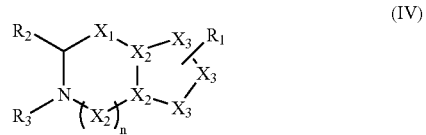

wherein
$X_1$ is $(CH_2)_m$ or $X_3$;
$X_2$ is independently $CH_2$, CH, or N;
$X_3$ is independently $(CH_2)$, CH, NH, N, O, C=O, C=S, S, S=O, or $SO_2$;
$R_1$ is an amino acid side chain moiety comprising at least one aryl, aralkyl or heteroaryl ring, and preferably comprising a fused bicyclic ring;
$R_2$ is a hydrogen bonding or cationic amino acid side chain moiety;
$R_3$ is an amino acid or dipeptide, optionally further comprising an amine capping group, wherein at least one amino acid residue comprises a substituted or unsubstituted aryl or aralkyl, preferably wherein the at least one amino acid residue comprising a substituted or unsubstituted aryl or aralkyl is a D-amino acid residue;
m is 0 or 1; and
n is 0, 1, or 2;

provided that any two adjacent CH groups, adjacent NH and CH groups or adjacent NH groups may optionally form a double bond.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist peptidomimetic compound of this invention can accordingly be used as a therapeutic chemoprevention agent for combating harmful sun or UV exposure that induces neoplastic activity in skin melanocytes.

In another embodiment compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia or cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with maturity-onset obesity syndrome associated with hyperphagia, hyperinsulinemia and hyperglycemia.

In yet another embodiment, compounds of this invention may used as therapeutic agents for treatment of sexual dysfunction, including treatment of both male erectile dysfunction and female sexual dysfunction. In yet another embodiment, compounds of this invention may be used as therapeutic agents for treatment of inflammation, including specifically MC1-R and MC3-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

In general, the actual quantity of compound of this invention administered to a patient will vary between fairly wide ranges depending upon the mode of administration, the formulation used, and the response desired. This may readily be determined by one of ordinary skill in the art through means such as pharmacokinetic studies, plasma half-life studies, dose escalation studies, and the like.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to induce the desired therapeutic effect.

In general, the compounds of this invention are highly active, with dose responses as low as 0.01 μg/kg, generally with optimal or peak dose responses between about 0.1 μg/kg and 25 μg/kg, depending on the specific compound and the route of administration. For example, the compound can be administered at 0.01, 0.05, 0.1, 0.5, 1, 5, 10, 50, 100, or 500 μg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction. In an especially preferred embodiment of combination therapy the sexual dysfunction is erectile dysfunction. In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a compound of this invention and 2) a compound that is a melanocortin receptor agonist. The present invention further provides pharmaceutical compositions that comprise 1) a compound of this invention; 2) a compound that is a melanocortin receptor agonist; and 3) a third compound useful for the treatment of sexual dysfunction. The present invention also provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777-1784 (1996); and R. A. H. Adan, Identification of Antagonists for Melanocortin MC3, MC4, and MC5 Receptors. *Eur. J. Pharmacol.*, 269:331-337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)—OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or U.S. 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; a-adrenergic antagonists; dopanergic ligands; androgens; selective androgen receptor modulators (SARMs); buprorion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (–)-cis-6-phenyl-5-[-4-(2-pyrrolidin-1-yl-ethoxy)-phenyl]-5,6,7, 8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices. The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)--N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (–) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be explored include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™. Capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists for example certain compounds in U.S. Pat. No. 4,626,549 which is incorporated by reference herein, α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention, can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

The invention is further illustrated by the following non-limiting examples.

EXAMPLE 1

General procedure for the synthesis of substituted hexahydropyrrolo[1,2-a]imidazol-3-one The general method is shown in Scheme 1. TBTU (1 eq) was added to a solution of N-(tert-butoxycarbonyl)-glutamine benzyl ester and NMM (1 eq) in dry DCM and the mixture stirred at room temperature for 30 minutes. A mixture of N,O-dimethylhydroxyamine hydrochloride (1.5 eq) and NMM (1.5 eq) in DCM was separately stirred for 30 minutes. These two mixtures were combined and stirred at room temperature for 18 hours. The organic solvent was evaporated, the residue was loaded on a flash chromatograph column and eluted with ethyl acetate/hexane (v/v=$^2$/$_1$) to give N-(tert-butoxycarbonyl)-5-(N,O-dimethyl-hydroxamide)-glutamine benzyl ester. N-(tert-butoxycarbonyl)-5-(N,O-dimethyl-hydroxyamide)-glutamine benzyl ester and a catalytic amount of palladium (10%) in carbon taken in methanol was stirred under 1 atm. hydrogen overnight at room temperature. After filtration and evaporation of solvent, a clear oily product was obtained which was used as is in next step.

To a solution of N-(tert-butoxycarbonyl)-5-(N,O-dimethyl-hydroxamide)-glutamine (3.9 g, 13.45 mmol) and NMM (1 eq) in THF at −15° C. was slowly added a THF solution of isobutyl chloroformate (1 eq). The mixture was stirred at this temperature for an additional 30 minutes. A solution of sodium borohydride (1.5 eq) in water was added in portions to the THF solution. After 20 minutes, the temperature was raised to room temperature and stirred for another 1 hour. The organic solvent was evaporated and the residue was purified on a column (10% methanol in DCM) to give N-(tert-butoxycarbonyl)-5-(N,O-dimethyl-hydroxamide)-glutaminol.

To N-(tert-butoxycarbonyl)-5-(N,O-dimethyl-hydroxamide)-glutaminol and TEA (2 eq) in DCM at 0° C. was added methanesulfonyl chloride (2 eq) also in DCM. The solution was stirred at 0° C. for 20 minutes and at room temperature for an additional 45 minutes. The solvent was evaporated and the product extracted from water with ethyl acetate. The organic layer was washed with water and brine and dried over sodium sulfate. After removing solvent, the yield of mesylated product approached 100%.

Sodium hydride (1.5 eq) was washed with hexane, the hexane was decanted and dry DMF was added. The suspension was mixed slowly with an aromatic alcohol (1.5 eq) at room temperature and the solution was stirred for 1 hour until no hydrogen was released. The mesylated compound in DMF was mixed with the above compound and stirred at room temperature for 24 hours. The solution was subsequently heated at 90° C. for an additional 24 hours. After cooling, the solution was poured into water and extracted twice with ethyl acetate. The combined organic layer was washed with water and brine and dried over sodium sulfate. The organic solvent was removed and the residue was purified on a silica gel column eluted by ethyl acetate/hexane (v/v=2/1) to give O-alkylated N-(tert-butoxycarbonyl)-5-(N,O-dimethyl-hydroxamide)-glutaminol.

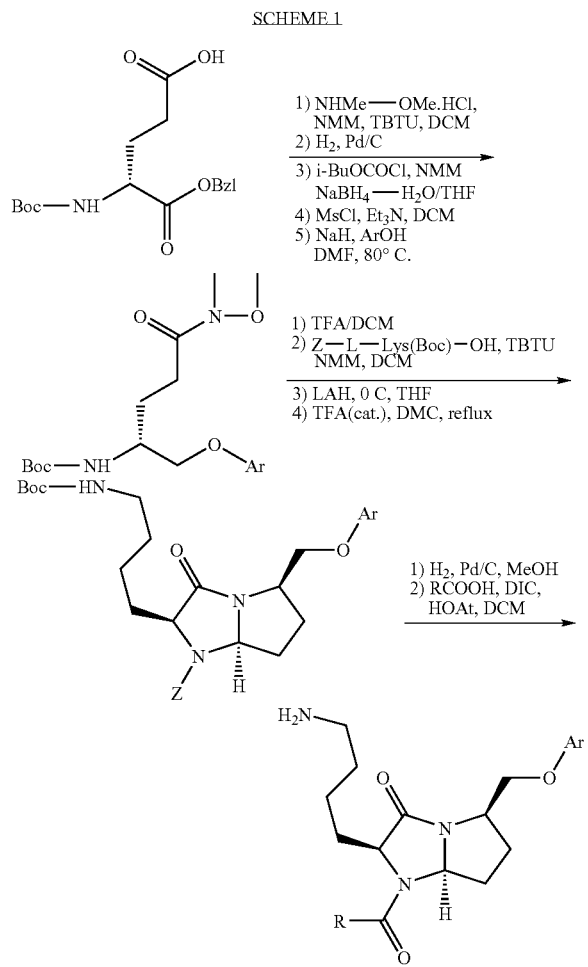

SCHEME 1

The compound synthesized in the preceding step was stirred in TFA/DCM (v/v=1/4) for 1 hour. The solvent was removed and residue dried under vacuum. The residue was mixed with NMM (4 eq) in DCM. Separately, a DCM solution of Z-Lys(Boc)—OH (2 eq) and NMM (2 eq) was mixed with TBTU (2 eq) and stirred for 30 minutes. These two solutions were combined and stirred overnight at room temperature. After evaporating solvent and purification on an ethyl acetate column, O-alkylated N-(N-benzyloxy-N'-tert-butoxycarbonyl-L-lysyl)-5-(N,O-dimethyl-hydroxamide)-glutaminol was obtained in purified form.

O-alkylated N-(N-benzyloxycarbonyl-N'-tert-butoxycarbonyl-L-lysyl)-5-(N,O-dimethyl-hydroxamide)-glutaminol was dissolved in dry THF. The solution was cooled to 0° C. under nitrogen atmosphere. To this solution was slowly added LAH (1 M in THF, 1.25 eq). The solution was stirred at this temperature for 30 minutes and the reaction stopped by adding potassium hydrogen sulfate (1.5 eq) in water. After stirring for 30 minutes the solvent was removed and the residue re-dissolved in ether. The organic phase was washed with 1 N hydrochloric acid, saturated sodium hydrogen carbonate and brine. The ether layer was dried over sodium sulfate. Solvent was removed to yield an aldehyde derivative which was used for the next reaction without further purification.

The aldehyde derivative was dissolved in DCM containing a catalytic amount of TFA and the solution refluxed for 5 hours. After removing solvent, the residue was purified on a column with DCM/acetone (v/v=8/1) to give 2,5-substituted 1-benzyloxycarbonyl-hexahydro-pyrrolo[1,2-a]imidazol-3-one.

2,5-substituted 1-benzyloxycarbonyl-hexahydro-pyrrolo[1,2-a]imidazol-3-one was dissolved in methanol and a catalytic amount of palladium (10%) on carbon was added. The mixture was stirred under hydrogen (1 atm.) overnight. After filtration and evaporation of solvent, the residue was dried under vacuum to give 2,5-substituted hexahydro-pyrrolo[1,2-a]imidazol-3-one. A DMF solution containing a desired Fmoc protected amino acid (2 eq) and HOAt (2 eq) was mixed with DIC (2 eq), stirred for 10 minutes and added to the 2,5-substituted hexahydro-pyrrolo[1,2-a]imidazol-3-one. After 24 hours at room temperature, DMF was removed and the residue was purified on a silica gel column to give 2,5-substituted hexahydro-pyrrolo[1,2-a]imidazol-3-one coupled at 1-position with the Fmoc protected amino acid. The Fmoc group was removed by stirring the compound in diethyl amine/ethyl acetate (v/v=1/4) at room temperature for 12 hours. The solvent was removed under vacuum to yield a residue that was used without further purification. It was mixed with a reaction mixture obtained separately by treating a desired substituted acid (2 eq) and NMM (2 eq) with TBTU (2 eq) in DMF for 10 minutes. The combined reaction mixture was stirred for an additional 24 hours. The solvent was removed and the final fully protected compound was purified by flash chromatography. In appropriate instances, Fmoc groups were removed by treatment with 20% diethyl amine in ethyl acetate while Boc groups were removed by treatment with 30% TFA in DCM for 1 hour. The final compounds were obtained in pure form after purification by HPLC.

An alternate method is shown in Scheme 2. Purified O-alkylated N-(tert-butoxycarbonyl)-5-(N,O-dimethyl-hydroxamide)-glutaminol synthesized as above was stirred in TFA/DCM (v/v=1/4) for 1 hour. The solvent was removed and residue dried under vacuum. The residue was mixed with NMM (4 eq) in DCM. Separately, a DCM solution of Z-Arg(Boc)$_2$—OH (2 eq) and NMM (2 eq) was mixed with TBTU (2 eq) and stirred for 30 minutes. These two solutions were combined and stirred overnight at room temperature. After evaporating solvent the residue was purified on a column using ethyl acetate as eluant, O-alkylated N-(N-benzyloxy-N'-tert-butoxycarbonyl-L-lysyl)-5-(N,O-dimethyl-hydroxamide)-glutaminol was obtained in purified form. The reaction then proceeded as above.

SCHEME 2

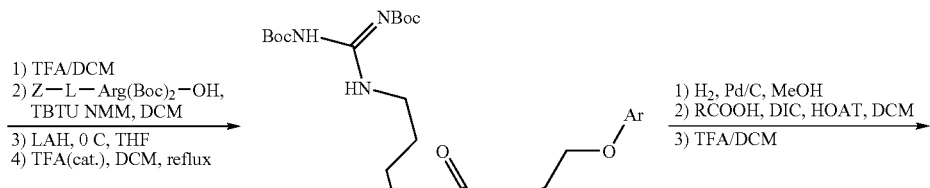

EXAMPLE 2

Alternative procedure for the synthesis of substituted hexahydro-pyrrolo[1,2-a]imidazol-3-one The general method is shown in Scheme 3. To N-(tert-butoxycarbonyl)-L-naphtylalanine and NMM (1 eq) in dry DCM was added TBTU (1 eq). The mixture was stirred at room temperature for 30 minutes. A mixture of N,O-dimethylhydroxyamine hydrochloride (1.5 eq) and NMM(1.5 eq) in DCM was stirred for 30 minutes. These two mixtures were combined and stirred at room temperature for 18 hours. The organic solvent was evaporated and the residue was purified by flash chromatography to give N-(tert-butoxycarbonyl)-naphtylalanine N,O-dimethyl-hydroxamide.

N-(tert-butoxycarbonyl)-napthylalanine N,O-dimethyl-hydroxamide was dissolved in dry THF, and the solution was cooled to 0° C. under nitrogen atmosphere. LAH (1 M in THF, 1.25 eq) was added to the solution slowly and stirred at this temperature for 30 minutes. The reaction was stopped by adding potassium hydrogen sulfate (1.5 eq) in water. After stirring for 30 minutes, the solvent was removed and the residue dissolved in ether. The organic phase was washed with 1 N hydrochloric acid, saturated sodium hydrogen carbonate and brine. The ether layer was dried over sodium sulfate. Solvent was removed to give an aldehyde derivative A.

SCHEME 3

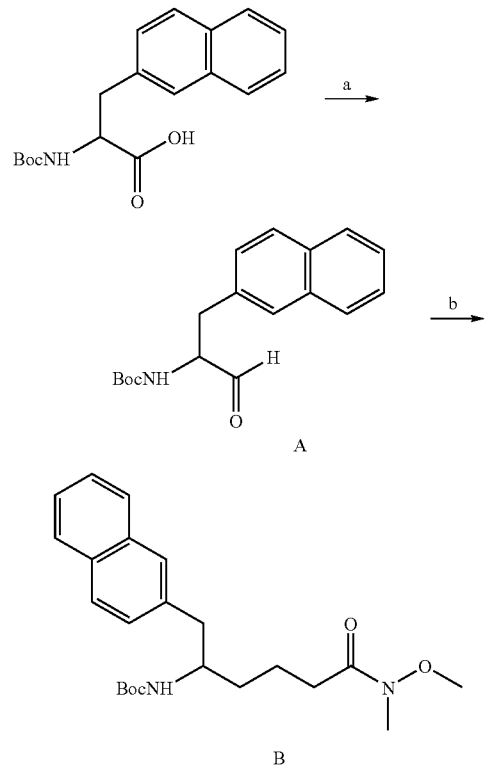

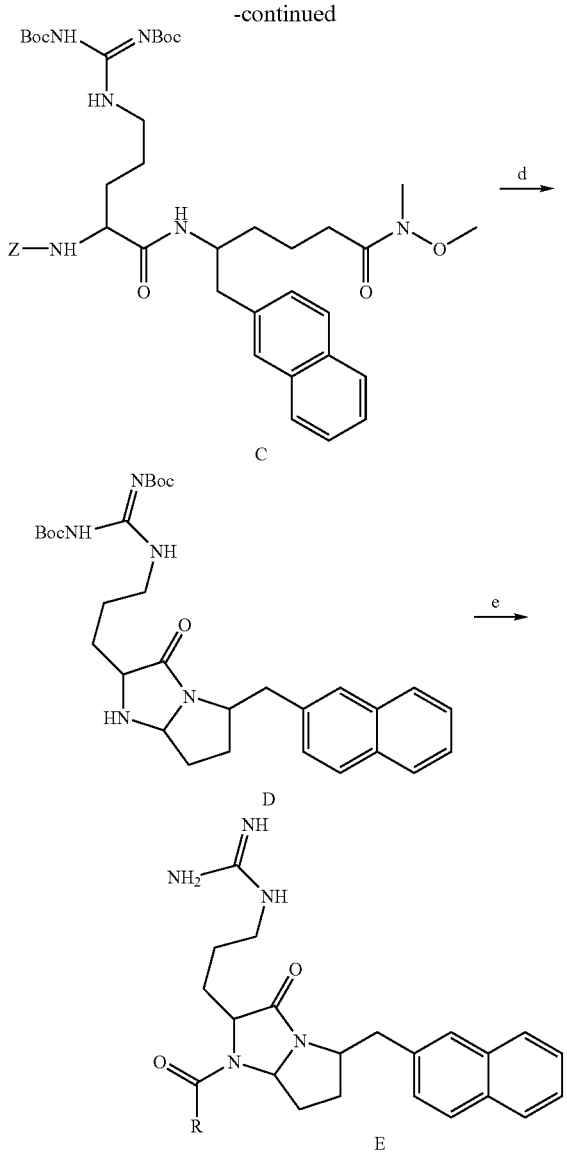

Reagents: (a) i) TBTU, NMM, MeNHOMe, DCM; ii) LAH, THF;
(b) i) Ph₃P=CH₂CONMeOMe, DCM; ii) Pd/C, H₂, MeOH; (c) i) TFA/DCM;
ii) Z—Arg(Boc)₂—OH, TBTU, NMM, DCM; (d) i) TFA (cat.), DCM, reflux;
ii) Pd/C, H₂, MeOH; (e) i) RCOOH, HOAt, DIC; ii) TFA/DCM.

Compound A and N-methoxy-N-methyl-2-(triphenylphosphoranylidene) acetamide (2 eq) in methylene chloride were stirred for 16 hours. The solvent was evaporated and the residue was purified on a silica gel column to give a compound mainly with (E)-olefin. This compound was subsequently subjected to treatment with hydrogen with catalytic amounts of palladium on carbon (10%) in ethyl acetate for 10 hours. After filtration and evaporation of solvent, compound B was obtained.

Compound B was treated with 25% TFA in methylene chloride for one hour, and the solvent was removed. The compound was neutralized by NMM, which was then added to the mixture of Z-Arg(Boc)₂—OH, NMM (1 eq) and TBTU (1 eq) in dry DCM. The reaction was carried out for 16 hours at room temperature. Solvent was removed and the residue was purified on silica gel column to give compound C.

Compound C was dissolved in dry THF. The solution was cooled to 0° C. under nitrogen atmosphere. LAH (1 M in THF, 1.25 eq) was added to this solution slowly. The solution was stirred at this temperature for 30 minutes and the reaction was stopped by adding potassium hydrogen sulfate (1.5 eq) in water. After stirring for 30 minutes, the solvent was removed and re-dissolved in ether. The organic phase was washed with 1 N hydrochloric acid, saturated sodium hydrogen carbonate and brine, and the ether layer was dried over sodium sulfate. Solvent was removed to give an aldehyde derivative, which was used for the next step reaction without further purification.

The aldehyde derivative was dissolved in DCM containing catalytic amounts of TFA and the solution was refluxed for 5 hours. After removing the solvent the residue was purified on a column to give Cbz-protected compound D, which was dissolved in methanol in the presence of catalytic amounts of palladium on carbon (10%). The mixture was stirred under hydrogen (1 atm.) overnight. After filtration and evaporation of solvent, the residue was dried under vacuum to give compound D.

Compound D was coupled with desired amino acids (2 eq) by use of HOAt (2 eq) and DIC (2 eq) in DMF solution overnight at room temperature. Flash chromatography (ethyl acetate/hexane=2) produced the product with protection groups. The Fmoc group was removed by treatment with 20% diethyl amine in ethyl acetate and the Boc group removed by treatment with 30% TFA in methylene chloride for 1 hour as applicable to the compounds. The final pure compounds were obtained by purification on HPLC.

EXAMPLE 3

Competitive inhibition assay

A competitive inhibition binding assay was conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM MgCl₂, 2 mM CaCl₂, and 5 mM KCl, at pH 7.2. The assay tube also contained a chosen concentration of the test compound of this invention, typically a 1 μM concentration, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 μM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in presence of test compounds were normalized with respect to 100% specific binding to determine the percent inhibition of $^{125}$I-NDP-α-MSH binding. Each assay was conducted in triplicate and the actual mean values are described.

EXAMPLE 4

EC₅₀ determination in functional activity assay

The Ki (nM) of certain compounds of the invention were determined. Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, were plated in 96 well plates at a density of $0.5 \times 10^5$ cells per well. Cells were incubated with the test compounds in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software.

EXAMPLE 5

Functional status

The agonist/antagonist status with respect to MC1-R, MC4-R and MC5-R of certain compounds of the invention was determined. Antagonistic activity was determined by measuring the inhibition of α-MSH-induced cAMP levels following exposure to the compounds as in Example 4.

EXAMPLE 6

Penile erection induction

The ability of compounds to induce penile erection (PE) in male rats was evaluated with selected compounds. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with compounds at a variety of doses via intravenous (IV) or intracerebroventricular (ICV) routes. Immediately after treatment, rats were placed into individual polystyrene cages (27 cm long, 16 cm wide, and 25 cm high) for behavioral observation. Rats were observed for 30 minutes (IV) or 90 minutes (ICV) and the number of yawns, grooming bouts and PEs were recorded in 10-minute bins.

EXAMPLE 7

ICV food intake and body weight change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed ICV with vehicle or selected compounds (1-3 nmol). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 8

IV food intake and body weight change

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed IV with vehicle or selected compounds (0.5-3 mg/kg). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 9

Determination of mass and nuclear magnetic resonance analysis

The mass values were determined using a Waters MicroMass ZQ device utilizing a positive mode. Mass determinations were compared with calculated values and expressed in the form of mass weight plus one (M+1).

Proton NMR data was obtained using a Bruker 300 MHz spectrometer. The spectra were obtained after dissolving compounds in a deuteriated solvent such as chloroform, dimethyl sulfoxide, or methanol as appropriate.

EXAMPLE 10

A compound of the following structure:

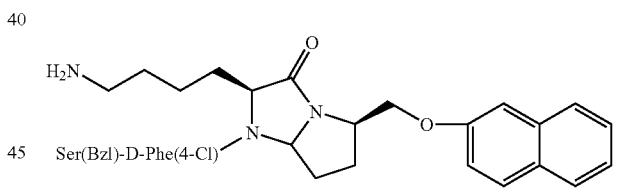

was synthesized by the general method of scheme 1 as set forth in Example 1. The molecular weight was determined to be 712.3 ESI-MS (M+1) by the method of Example 9. ($^1$H NMR, $CD_3OD$) δ: 1.0-1.8 (m, 6H), 2.2 (m, 2H), 2.5 (m, 2H), 2.7 (m, 2H), 3.0 (m, 2H), 3.7 (m, 2H), 4.1 (m, 2H), 4.3-4.5 (m, 3H), 4.6 (m, 2H), 5.1 (m, H), 5.3 (m, H), 7.1-7.9 (m, 16H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 90% | 14% | 81% | 86% |

EXAMPLE 11

A compound of the following structure:

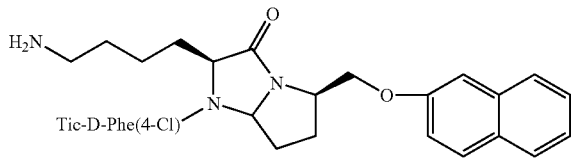

was synthesized by the general method of scheme 1 as set forth in Example 1. The molecular weight was determined to be 694.0 ESI-MS(M+1) by the method of Example 9. ($^1$H NMR, CD$_3$OD) δ: 1.0-1.8 (m, 6H), 2.2 (m, 2H), 2.5 (m, 2H), 2.7 (m, 2H), 2.9 (m, 2H), 3.2 (m, 2H), 4.2 (m, 2H), 4.2-4.4 (m, 3H), 4.4 (m, 2H), 5.1 (m, H), 5.4 (m, H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 µM | | | |
|---|---|---|---|
| MC1-R | MC3-R | MC4-R | MC5-R |
| 95% | 24% | 94% | 73% |

In a cAMP assay as in Example 5 for determination of agonist/antagonist status, it was determined that the compound was an agonist as to MC4-R. The Ki was determined by the method of Example 4, with the following results:

| Ki (nM) | | | |
|---|---|---|---|
| MC1-R | MC3-R | MC4-R | MC5-R |
| 10 | 787 | 24 | 398 |

EXAMPLE 12

A compound of the following structure:

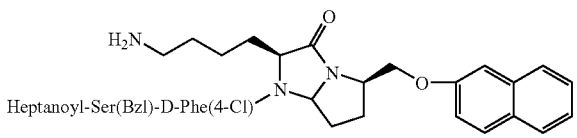

was synthesized by the general method of scheme 1 as set forth in Example 1. The molecular weight was determined to be 824.2 ESI-MS(M+1) by the method of Example 9. ($^1$H NMR, CD$_3$OD) δ: 0.9 (m, 3H), 1.1-1.8 (m, 14H), 2.1 (m, 2H), 2.2 (m, 2H), 2.5 (m, 2H), 2.7 (m, 2H), 3.0 (m, 2H), 3.7 (m, 2H), 4.2 (m, 2H), 4.3-4.5 (m, 3H), 4.6 (m, 2H), 5.1 (m, H), 5.3 (m, H), 7.1-7.9 (m, 16H). Competitive inhibition testing of the compound against $^{125}$I-NDP-α-MSH following the methods of Example 3 yielded the following results (average of triplicates with actual mean values described):

| Inhibition at 1 µM | | | |
|---|---|---|---|
| MC1-R | MC3-R | MC4-R | MC5-R |
| 98% | 75% | 98% | 95% |

In a cAMP assay as in Example 5 for determination of agonist/antagonist status, it was determined that the compound was an antagonist as to MC4-R. The Ki was determined by the method of Example 4, with the following results:

| Ki (nM) | | | |
|---|---|---|---|
| MC1-R | MC3-R | MC4-R | MC5-R |
| 13 | 181 | 22 | 116 |

EXAMPLE 13

A compound of the following structure:

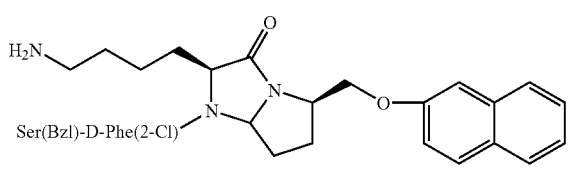

was synthesized by the general method of scheme 1 as set forth in Example 1. The molecular weight was determined to be 711.9 ESI-MS(M+1) by the method of Example 9. ($^1$H NMR, CD$_3$OD) δ: 1.0-1.8 (m, 6H), 2.1 (m, 2H), 2.4 (m, 2H), 2.7 (m, 2H), 3.1 (m, 2H), 3.6 (m, 2H), 4.1 (m, 2H), 4.2-4.4 (m, 3H), 4.5 (m, 2H), 5.1 (m, H), 5.3 (m, H), 7.1-7.9 (m, 16H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 28% | 0% | 60% | 38% |

EXAMPLE 14

A compound of the following structure:

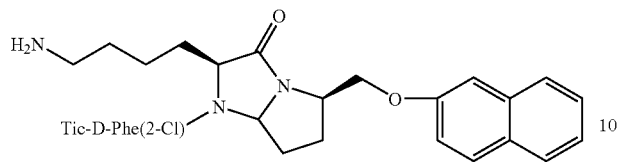

Tic-D-Phe(2-Cl)

was synthesized by the general method of scheme 1 as set forth in Example 1. The molecular weight was determined to be 694.3 ESI-MS(M+1) by the method of Example 9. ($^1$H NMR, CD$_3$OD) δ: 1.0-1.8 (m, 6H), 2.2 (m, 2H), 2.4 (m, 2H), 2.7 (m, 2H), 2.8 (m, 2H), 3.2 (m, 2H), 4.2 (m, 2H), 4.2-4.4 (m, 3H), 4.4 (m, 2H), 5.2 (m, H), 5.4 (m, H), 7.1-7.9 (m, 15H). Competitive inhibition testing of the compound against $^{125}$I-NDP-α-MSH following the methods of Example 3 yielded the following results (average of triplicates with actual mean values described):

| | Inhibition at 1 μM | | |
|---|---|---|---|
| MC1-R | MC3-R | MC4-R | MC5-R |
| 42% | 2% | 89% | 38% |

EXAMPLE 15

A compound of the following structure:

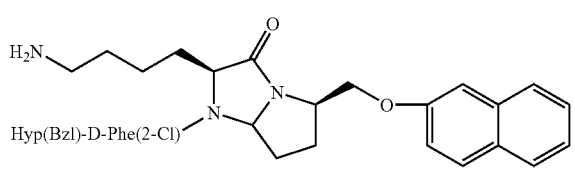

Hyp(Bzl)-D-Phe(2-Cl)

was synthesized by the general method of scheme 1 as set forth in Example 1. The molecular weight was determined to be 738.0 ESI-MS(M+1) by the method of Example 9. ($^1$H NMR, CD$_3$OD) δ: 1.0-2.0 (m, 6H), 2.2 (m, 2H), 2.3-2.9 (m, 6H), 3.2 (m, 2H), 3.4 (m, 2H), 4.2 (m, 2H), 4.2-4.4 (m, 3H), 4.6 (m, 2H), 5.2 (m, H), 5.4 (m, H), 7.1-7.9 (m, 16H). Competitive inhibition testing of the compound against $^{125}$I-NDP-60-MSH following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 44% | 0% | 74% | 37% |

EXAMPLE 16

A compound of the following structure:

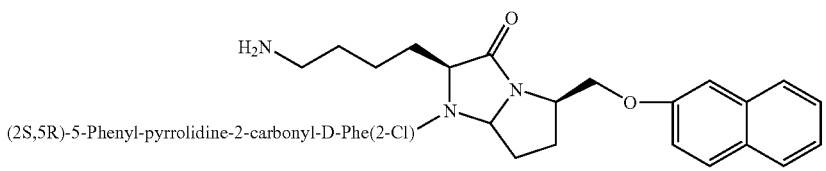

(2S,5R)-5-Phenyl-pyrrolidine-2-carbonyl-D-Phe(2-Cl)

was synthesized by the general method of scheme 1 as set forth in Example 1. The molecular weight was determined to be 707.9 ESI-MS(M+1) by the method of Example 9. ($^1$H NMR, CD$_3$OD) δ: 1.0-1.8 (m, 6H), 2.1 (m, 2H), 2.2-2.9 (m, 1OH), 3.2 (m, 2H), 4.2 (m, 2H), 4.2-4.7 (m, 4H), 5.3 (m, H), 5.5 (m, H), 7.1-7.9 (m, 16H). Competitive inhibition testing of the compound against $^{125}$I-NDP-α-MSH following the methods of Example 3 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 4% | 0% | 44% | 13% |

EXAMPLE 17

A compound of the following structure:

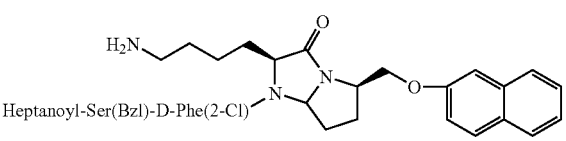

Heptanoyl-Ser(Bzl)-D-Phe(2-Cl)

was synthesized by the general method of scheme 1 as set forth in Example 1. The molecular weight was determined to be 824.0 ESI-MS(M+1) by the method of Example 9. Competitive inhibition testing of the compound against $^{125}$-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 71% | 30% | 82% | 47% |

EXAMPLE 18

A compound of the following structure:

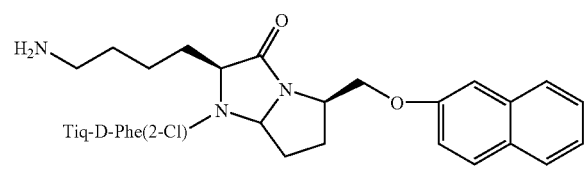

Tiq-D-Phe(2-Cl)

was synthesized by the general method of scheme 1 as set forth in Example 1. The molecular weight was determined to be 694.2 ESI-MS(M+1) by the method of Example 9. ($^1$H NMR, CD$_3$OD) δ: 1.0-1.8 (m, 6H), 2.15 (m, 1H), 2.35 (m, 1H), 2.45 (m, 1H), 2.65-2.9 (m, 3H), 3.1 (m, 3H), 3.4 (m, 3H), 3.65 (m, 1H), 4.2 (m, 1H), 4.3-4.6 (m, 3H), 5.0-5.55 (m, 3H), 6.8-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 66% | 8% | 57% | 46% |

EXAMPLE 19

A compound of the following structure:

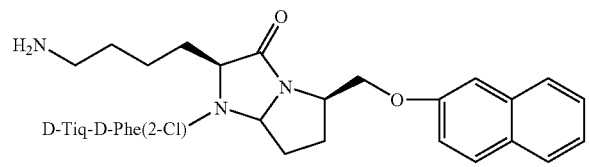

D-Tiq-D-Phe(2-Cl)

was synthesized by the general method of scheme 1 as set forth in Example 1. The molecular weight was determined to be 694.2 ESI-MS(M+1) by the method of Example 9. ($^1$H NMR, CD$_3$OD) δ: 1.0-1.8 (m, 6H), 2.15 (m, 2H), 2.4 (m, 2H), 2.7 (m, 4H), 3.15 (m, 3H), 3.45 (m, 3H), 3.75 (m, 1H), 4.15 (m, 1H), 4.2-4.5 (m, 3H), 5.0-5.55 (m, 3H), 6.8-7.9 (m, 15H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 48% | 0% | 37% | 20% |

EXAMPLE 20

A compound of the following structure:

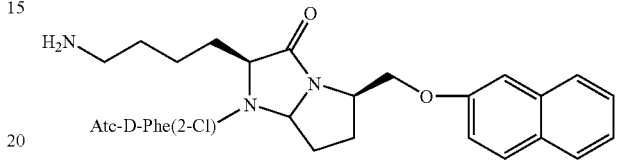

Atc-D-Phe(2-Cl)

was synthesized by the general method of scheme 1 as set forth in Example 1. The molecular weight was determined to be 708.2 ESI-MS(M+1) by the method of Example 9. ($^1$H NMR, CD$_3$OD) δ: 1.0-2.0 (m, 8H), 2.1-2.5 (m, 4H), 2.7 (m, 2H), 2.9-3.1 (m, 4H), 3.4 (m, 1H), 3.6 (m, 1H), 4.15 (m, 1H), 4.25-4.5 (m, 3H), 5.05 (m, 1H), 5.35 (m, 2H), 6.8-7.9 (m, 15H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 24% | 0% | 34% | 22% |

EXAMPLE 21

A compound of the following structure:

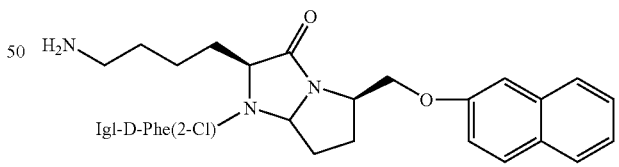

Igl-D-Phe(2-Cl)

was synthesized by the general method of scheme 1 as set forth in Example 1. The molecular weight was determined to be 708.2 ESI-MS(M+1) by the method of Example 9. ($^1$H NMR, CD$_3$OD) δ: 1.1-2.0 (m, 6H), 2.2 (m, 2H), 2.5 (m, 2H), 2.65-2.9 (m, 6H), 3.05 (m, 1H), 3.25 (m, 1H), 3.95 (m, 1H), 4.2 (m, 1H), 4.3-4.5 (m, 3H), 5.0-5.5 (m, 3H), 6.8-7.9 (m, 15H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 10% | 0% | 12% | 46% |

EXAMPLE 22

A compound of the following structure:

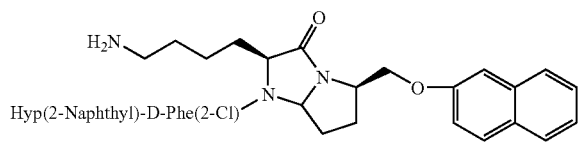

Hyp(2-Naphthyl)-D-Phe(2-Cl)

was synthesized by the general method of scheme 1 as set forth in Example 1. The molecular weight was determined to be 774.2 ESI-MS(M+1) by the method of Example 9. ($^1$H NMR, CD$_3$OD) δ: 1.1-2.0 (m, 6H), 2.0-2.9 (m, 8H), 2.95 (m, 1H), 3.15 (m, 1H), 3.55 (m, 1H), 365 (m, 1H), 4.15 (m, 1H), 4.3-4.5 (m, 3H), 5.0-5.4 (m, 3H), 6.75-7.9 (m, 16H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 21% | 0% | 0% | 17% |

EXAMPLE 23

A compound of the following structure:

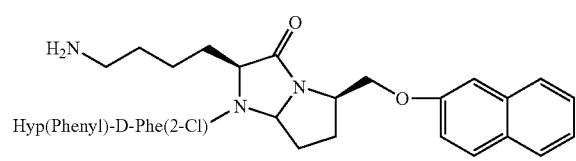

Hyp(Phenyl)-D-Phe(2-Cl)

was synthesized by the general method of scheme 1 as set forth in Example 1. The molecular weight was determined to be 724.3 ESI-MS(M+1) by the method of Example 9. Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 µM | | | |
|---|---|---|---|
| MC1-R | MC3-R | MC4-R | MC5-R |
| 7% | 0% | 22% | 21% |

EXAMPLE 24

A compound of the following structure:

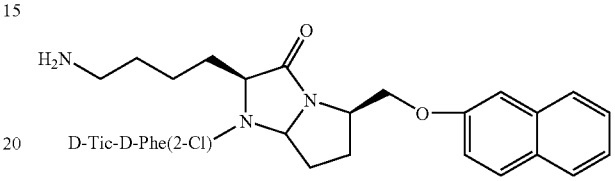

D-Tic-D-Phe(2-Cl)

was synthesized by the general method of scheme 1 as set forth in Example 1. The molecular weight was determined to be 694.2 ESI-MS(M+1) by the method of Example 1. ($^1$H NMR, CD$_3$OD) δ: 0.9-1.85 (m, 6H), 1.95-2.85 (m, 6H), 2.95 (m, 1H), 3.05-3.55 (m, 4H), 3.55 (m, 1H), 3.65 (m, 1H), 3.9-4.5 (m, 7H), 5.0-5.4 (m, 2H), 6.75-7.9 (m, 15H). Competitive inhibition testing of the compound against $^{125}$I-NDP-α-MSH following the methods of Example 3 yielded the following results (average of triplicates with actual mean values described):

| Inhibition at 1 µM | | | |
|---|---|---|---|
| MC1-R | MC3-R | MC4-R | MC5-R |
| 47% | 12% | 79% | 18% |

EXAMPLE 25

A compound of the following structure:

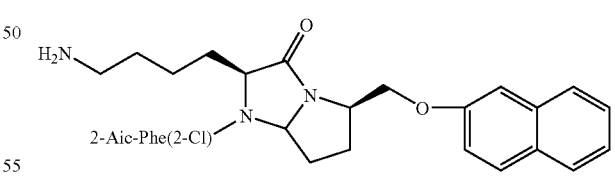

2-Aic-Phe(2-Cl)

was synthesized by the general method of scheme 1 as set forth in Example 1. The molecular weight was determined to be 693.9 ESI-MS(M+1) by the method of Example 9. ($^1$H NMR, CD$_3$OD) δ: 1.1-1.9 (m, 6H), 2.0-2.8 (m, 6H), 2.9-3.4 (m, 4H), 3.6 (m, 1H), 3.7(m, 1H), 4.15-4.5 (m, 3H), 5.0-5.4 (m, 3H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 26% | 2% | 36% | 28% |

EXAMPLE 26

A compound of the following structure:

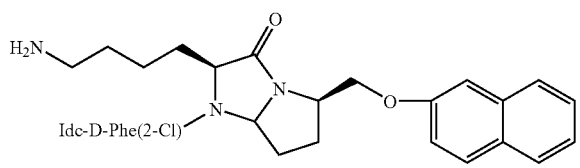

Idc-D-Phe(2-Cl)

was synthesized by the general method of scheme 1 as set forth in Example 1. The molecular weight was determined to be 679.9 ESI-MS(M+1) by the method of Example 9. ($^1$H NMR, CD$_3$OD) δ: 1.1-1.9 (m, 6H), 2.1-2.8 (m, 6H), 2.85-3.5(m, 4H), 4.05-4.5 (m, 3H), 5.0-5.4 (m, 3H), 6.75-7.9 (m, 15H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 34% | 0% | 47% | 14% |

EXAMPLE 27

A compound of the following structure:

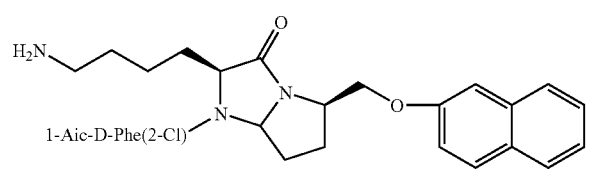

1-Aic-D-Phe(2-Cl)

was synthesized by the general method of scheme 1 as set forth in Example 1. The molecular weight was determined to be 694.2 ESI-MS(M+1) by the method of Example 9. ($^1$H NMR, CD$_3$OD) δ: 1.1-1.9 (m, 6H), 2.1-3.3 (m, 10 H), 4.1-4.5 (m, 3H), 5.0-5.4 (m, 2H), 6.8-7.9 (m, 15H). Competitive inhibition testing of the compound against $^{125}$-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 39% | 0% | 12% | 17% |

EXAMPLE 28

A compound of the following structure:

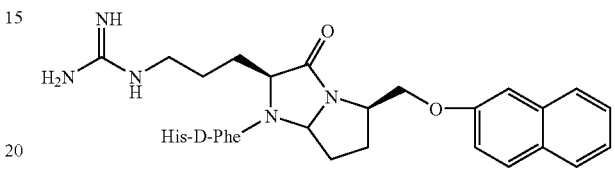

His-D-Phe was synthesized by the general method of scheme 1 as set forth in Example 1. The molecular weight was determined to be 666.1 ESI-MS(M+1) by the method of Example 9. ($^1$H NMR, CD$_3$OD) δ: 1.1-1.9 (m, 4H), 1.95-2.85 (m, 5H), 2.95-3.35(m, 5H), 3.9-4.4 (m, 5H), 4.7-5.4 (m, 2H), 6.75-7.9 (m, 14H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 99% | 30% | 69% | 28% |

In a functional assay as in Example 5, this compound was a full agonist at MC1-R. The Ki was determined by the method of Example 4, with the following results:

| Ki (nM) | | | |
|---|---|---|---|
| MC1-R | MC3-R | MC4-R | MC5-R |
| 1 | 963 | 226 | >1 μM |

EXAMPLE 29

A compound of the following structure:

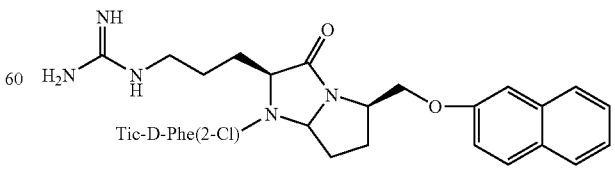

Tic-D-Phe(2-Cl)

was synthesized by the general method of scheme 2 as set forth in Example 1. The molecular weight was determined to be 722.2 ESI-MS(M+1) by the method of Example 9. ($^1$H NMR, CD$_3$OD) δ: 1.1-1.9 (m, 4H), 2.0-2.55 (m, 4H), 2.7-3.2 (m, 6H), 4.1-4.55 (m, 5H), 4.9-5.5 (m, 2H), 7.15-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 77% | 42% | 98% | 87% |

In a cAMP assay as in Example 5 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 81 | 756 | 9 | 301 |

EXAMPLE 30

A compound of the following structure:

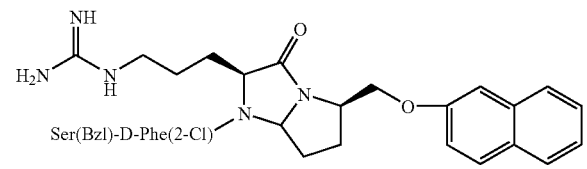

Ser(Bzl)-D-Phe(2-Cl)

was synthesized by the general method of scheme 2 as set forth in Example 1. The molecular weight was determined to be 740.0 ESI-MS(M+1) by the method of Example 9. ($^1$H NMR, CD$_3$OD) δ: 1.1-1.9 (m, 4H), 2.0-2.5 (m, 3H), 2.7-3.2 (m, 5H), 3.5 (m, 1H), 3.7 (m, 1H), 4.05-4.6 (m, 7H), 4.9-5.5 (m, 2H), 7.15-7.9 (m, 16H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 57% | 29% | 94% | 94% |

In a cAMP assay as in Example 5 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 121 | 733 | 41 | 151 |

EXAMPLE 31

A compound of the following structure:

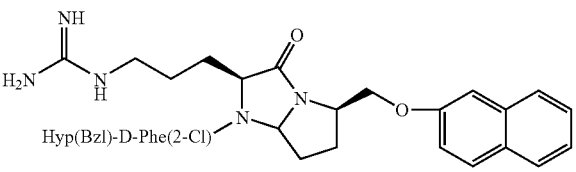

Hyp(Bzl)-D-Phe(2-Cl)

was synthesized by the general method of scheme 2 as set forth in Example 1. The molecular weight was determined to be 765.6 ESI-MS(M+1) by the method of Example 9. ($^1$H NMR, CD$_3$OD) δ: 1.2-1.95 (m, 4H), 2.0-2.95 (m, 6H), 2.0-3.2 (m, 4H), 3.4 (m, 1H), 3.5 (m, 1H), 4.1-4.55 (m, 7H), 4.9-5.5 (m, 2H), 7.15-7.9 (m, 16H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 54% | 40% | 95% | 93% |

In a cAMP assay as in Example 5 for determination of agonist/antagonist status, it was determined that the compound was an agonist as to MC1-R and MC4-R. The Ki was determined by the method of Example 4, with the following results:

| Ki (nM) | | | |
|---|---|---|---|
| MC1-R | MC3-R | MC4-R | MC5-R |
| 244 | 854 | 42 | 284 |

EXAMPLE 32

A compound of the following structure:

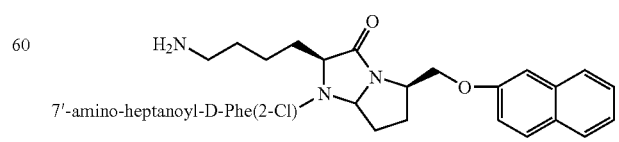

7'-amino-heptanoyl-D-Phe(2-Cl)

was synthesized by the general method of scheme 1 as set forth in Example 1. The molecular weight was determined to be 689.5 ESI-MS(M+1) by the method of Example 9. ($^1$H NMR, CD$_3$OD) δ: 1.2-2.0 (m, 12H), 2.0-2.95 (m, 6H), 2.1-3.3 (m, 12H), 4.0-4.5 (m, 4H), 4.9-5.5 (m, 2H), 7.15-7.9 (m, 11H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 95% | 6% | 81% | 36% |

EXAMPLE 33

A compound of the following structure:

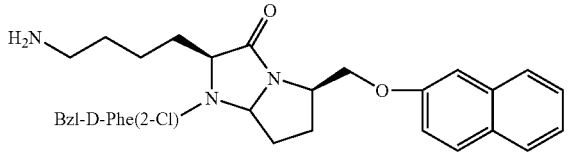

was synthesized by the general method of scheme 1 as set forth in Example 1. The molecular weight was determined to be 624.9 ESI-MS(M+1) by the method of Example 9. ($^1$H NMR, CD$_3$OD) δ: 1.0-1.75 (m, 6H), 1.85 (m, 1H), 2.15 (m, 1H), 2.3-2.8 (m, 4H), 3.3 (m, 2H), 3.6-4.6 (m, 7H), 4.8-5.5 (m, 1H), 7.1-7.9 (m, 16H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 11% | 13% | 16% | 14% |

EXAMPLE 34

A compound of the following structure:

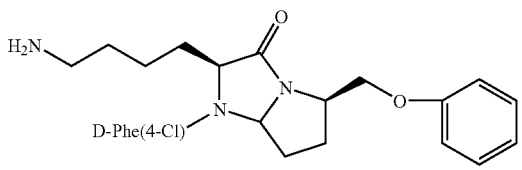

was synthesized by the general method of scheme 1 as set forth in Example 1. The molecular weight was determined to be 485.0 ESI-MS(M+1) by the method of Example 9. ($^1$H NMR, CD$_3$OD) δ: 1.0-1.75 (m, 6H), 1.85 (m, 1H), 2.15 (m, 1H), 2.25-2.8 (m, 4H), 3.2 (m, 2H), 3.65-4.55 (m, 5H), 4.8-5.5 (m, 1H), 6.9-8.0 (m, 9H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 9% | 0% | 0% | 0% |

EXAMPLE 35

A compound of the following structure:

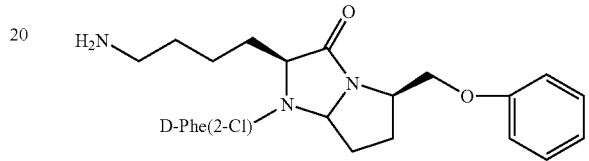

was synthesized by the general method of scheme 1 as set forth in Example 1. The molecular weight was determined to be 484.9 ESI-MS(M+1) by the method of Example 2. ($^1$H NMR, CD$_3$OD) δ: 1.1-1.85 (m, 6H), 1.9 (m, 1H), 2.15 (m, 1H), 2.25-2.85 (m, 4H), 3.35 (m, 2H), 3.6-4.6 (m, 5H), 4.8-5.5 (m, 1H), 6.9-8.0 (m, 9H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 0% | 4% | 0% | 0% |

EXAMPLE 36

A compound of the following structure:

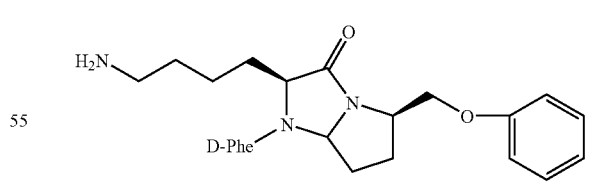

was synthesized by the general method of scheme 1 as set forth in Example 1. The molecular weight was determined to be 450.9 ESI-MS(M+1) by the method of Example 9. ($^1$H NMR, CD$_3$OD) δ: 1.1-1.75 (m, 6H), 1.85 (m, 1H), 2.15 (m, 1H), 2.45 (m, 1H), 2.65 (m, 1H), 2.8 (m, 2H), 3.2 (m, 2H), 3.4-4.5 (m, 5H), 4.6-5.5 (m, 1H), 6.9-7.5 (m, 10H). Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 1% | 4% | 0% | 0% |

EXAMPLE 37

A compound of the following structure:

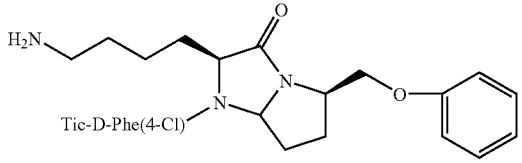

was synthesized by the general method of scheme 1 as set forth in Example 1. The molecular weight was determined to be 644.0 ESI-MS(M+1) by the method of Example 9. ($^1$H NMR, CD$_3$OD) δ: 1.0-1.85 (m, 6H), 2.15 (m, 2H), 2.35-2.85 (m, 4H), 3.0 (m, 2H), 3.15 (m, 2H), 4.0-4.5 (m, 6H), 4.8-5.4 (m, 2H), 6.9-7.5 (m, 13H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 81% | 19% | 51% | 25% |

EXAMPLE 38

A compound of the following structure:

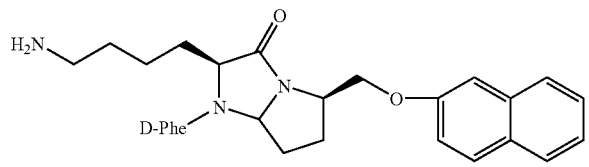

was synthesized by the general method of scheme 1 as set forth in Example 1. The molecular weight was determined to be 501.2 ESI-MS(M+1) by the method of Example 9. Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 46% | 13% | 0% | 1% |

EXAMPLE 39

A compound of the following structure:

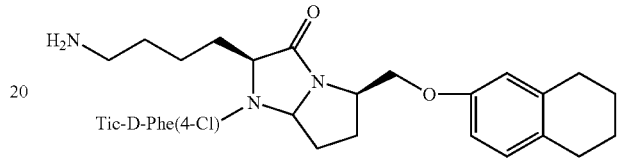

was synthesized by the general method of scheme 1 as set forth in Example 1. The molecular weight was determined to be 698.5 ESI-MS(M+1) by the method of Example 9. ($^1$H NMR, CD$_3$OD) δ: 1.0-1.9 (m, 1OH), 2.0-2.45 (m, 4H), 2.6-3.1 (m, 8H), 3.2 (m, 2H), 3.95-4.5 (m, 6H), 5.0-5.4 (m, 1H), 6.4-7.5 (m, 11H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 96% | 19% | 94% | 66% |

EXAMPLE 40

A compound of the following structure:

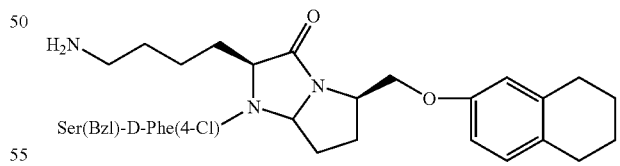

was synthesized by the general method of scheme 1 as set forth in Example 1. The molecular weight was determined to be 716.5 ESI-MS(M+1) by the method of Example 9. ($^1$H NMR, CD$_3$OD) δ: 1.0-1.9 (m, 10 H), 2.0-2.45 (m, 4H), 2.55-3.15 (m, 8H), 2.5-3.75 (m, 2H), 3.85-4.65 (m, 7H), 4.7-5.4 (m, 2H), 6.4-7.5 (m, 12H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 93% | 4% | 78% | 56% |

EXAMPLE 41

A compound of the following structure:

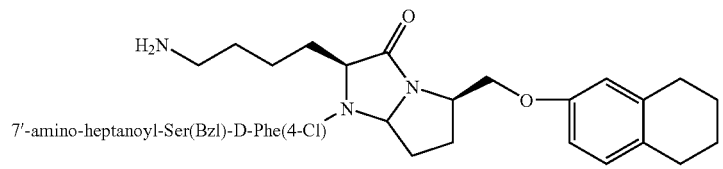

7'-amino-heptanoyl-Ser(Bzl)-D-Phe(4-Cl)

was synthesized by the general method of scheme 1 as set forth in Example 1. The molecular weight was determined to be 843.4 ESI-MS(M+1) by the method of Example 9. ($^1$H NMR, CD$_3$OD) δ: 1.0-1.9 (m, 18H), 2.0-3.05 (m, 16H), 3.7 (m, 2H), 3.9-4.65 (m, 7H), 4.7-5.4 (m, 2H), 6.4-7.5 (m, 12H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 97% | 59% | 96% | 84% |

EXAMPLE 42

A compound of the following structure:

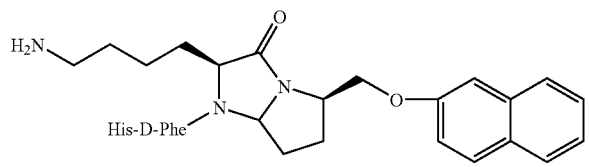

His-D-Phe was synthesized by the general method of scheme 1 as set forth in Example 1. The molecular weight was determined to be 658.1 ESI-MS(M+1) by the method of Example 9. Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 93% | 0% | 36% | 0% |

EXAMPLE 43

A compound of the following structure:

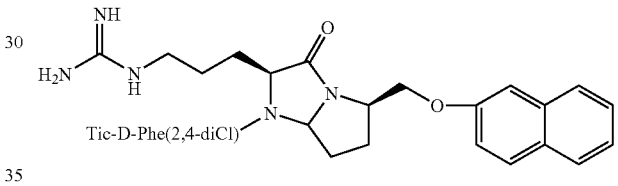

Tic-D-Phe(2,4-diCl)

was synthesized by the general method of scheme 2 as set forth in Example 1. The molecular weight was determined to be 757.2 ESI-MS(M+1) by the method of Example 9. ($^1$H NMR, CD$_3$OD) δ: 1.3-1.95 (m, 4H), 2.0-2.5 (m, 3H), 2.7-2.95 (m, 4H), 3.05-3.25 (m, 3H), 3.3 (m, 2H), 4.1-4.55 (m, 7H), 5.0-5.6 (m, 2H), 7.1-7.9 (m, 14H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 75% | 88% | 100% | 96% |

In a cAMP assay as in Example 5 for determination of agonist/antagonist status, it was determined that the compound was inactive as to MC1-R, and an antagonist as to MC4-R and MC5-R. The Ki was determined by the method of Example 4, with the following results:

| Ki (nM) | | | |
|---|---|---|---|
| MC1-R | MC3-R | MC4-R | MC5-R |
| 111 | 42 | 1 | 26 |

In ICV feeding studies as in Example 7 at 1 nmol dose levels, a 24 hour change in food intake of −5.4 g, and change in weight of −1.6 g, was observed.

In PE studies of male rats as in Example 6, IV administration at 1 μg/Kg produced a mean PE of 0.125, which is below baseline value.

EXAMPLE 44

A compound of the following structure:

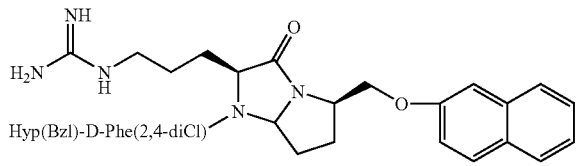

was synthesized by the general method of scheme 2 as set forth in Example 1. The molecular weight was determined to be 801.1 ESI-MS(M+1) by the method of Example 9. ($^1$H NMR, CD$_3$OD) δ: 1.3-1.95 (m, 4H), 2.0-2.7 (m, 4H), 2.55-3.15 (m, 4H), 3.3 (m, 2H), 3.5 (m, 2H), 4.1-4.65 (m, 7H), 5.0-5.6 (m, 2H), 7.1-7.9 (m, 15H) Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 53% | 84% | 100% | 100% |

In a cAMP assay as in Example 5 for determination of agonist/antagonist status, it was determined that the compound was an agonist as to MC1-R and MC5-R and an antagonist as to MC4-R.

EXAMPLE 45

A compound of the following structure:

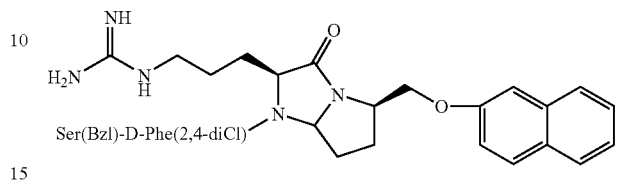

was synthesized by the general method of scheme 2 as set forth in Example 1. The molecular weight was determined to be 775.0 ESI-MS(M+1) by the method of Example 9. ($^1$H NMR, CD$_3$OD) δ: 1.3-1.95 (m, 4H), 2.0-2.5 (m, 3H), 2.65-3.2 (m, 5H), 3.5 (m, 1H), 3.7 (m, 1H), 3.75-4.65 (m, 7H), 5.0-5.6 (m, 2H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 53% | 77% | 100% | 94% |

In a cAMP assay as in Example 5 for determination of agonist/antagonist status, it was determined that the compound was an agonist as to MC1-R, MC4-R and MC5-R.

EXAMPLE 46

A compound of the following structure:

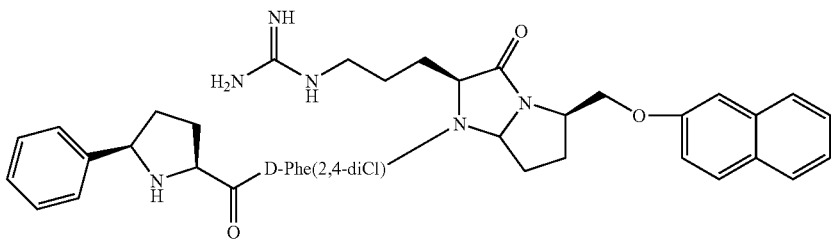

was synthesized by the general method of scheme 2 as set forth in Example 1. The molecular weight was determined to be 770.3 ESI-MS(M+1) by the method of Example 9. ($^1$H NMR, CD$_3$OD) δ: 1.3-1.95 (m, 4H), 2.0-2.55 (m, 6H), 2.75-3.3 (m, 6H), 4.1-4.7 (m, 5H), 5.1-5.6 (m, 2H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 16% | 43% | 97% | 86% |

In a cAMP assay as in Example 5 for determination of agonist/antagonist status, it was determined that the compound was an agonist as to MC1-R and MC5-R and an antagonist as to MC4-R. The Ki was determined by the method of Example 4, with the following results:

| Ki (nM) | | | |
|---|---|---|---|
| MC1-R | MC3-R | MC4-R | MC5-R |
| 1041 | 312 | 12 | 99 |

In ICV feeding studies as in Example 7 at 1 nmol dose levels, a 24 hour change in food intake of −9.52 g, and change in weight of −10.64 g, was observed.

EXAMPLE 47

A compound of the following structure:

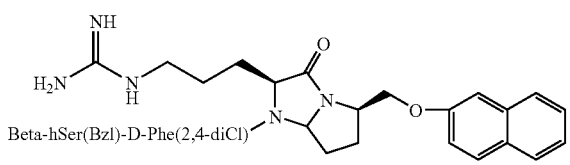

Beta-hSer(Bzl)-D-Phe(2,4-diCl)

was synthesized by the general method of scheme 2 as set forth in Example 1. The molecular weight was determined to be 788.3 ESI-MS(M+1) by the method of Example 9. ($^1$H NMR, CD$_3$OD) δ: 1.2-1.9 (m, 4H), 1.9-2.75 (m, 6H), 3.0-3.25 (m, 4H), 3.45 (m, 1H), 3.6 (m, 1H), 3.7 (m, 1H), 4.15-4.65 (m, 6H), 5.0-5.4 (m, 2H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 65% | 77% | 99% | 96% |

EXAMPLE 48

A compound of the following structure:

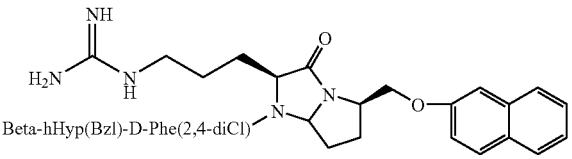

Beta-hHyp(Bzl)-D-Phe(2,4-diCl)

was synthesized by the general method of scheme 2 as set forth in Example 1. The molecular weight was determined to be 814.3 ESI-MS(M+1) by the method of Example 9. ($^1$H NMR, CD$_3$OD) δ: 1.3-1.95 (m, 4H), 2.0-2.5 (m, 4H), 2.6-3.25 (m, 8H), 3.35 (m, 1H), 3.45 (m, 1H), 4.05 (m, 1H), 4.15-4.65 (m, 7H), 4.9-5.5 (m, 2H), 7.1-7.9 (m, 15H). Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 59% | 88% | 99% | 95% |

EXAMPLE 49

A compound of the following structure:

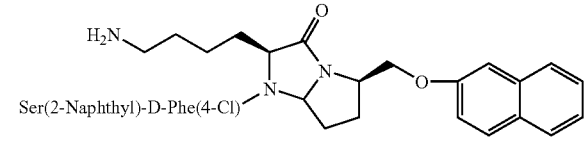

Ser(2-Naphthyl)-D-Phe(4-Cl)

was synthesized by the general method of scheme 2 as set forth in Example 1. The molecular weight was determined to be 762.4 ESI-MS(M+1) by the method of Example 9. Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 51% | 23% | 53% | 54% |

EXAMPLE 50

A compound of the following structure:

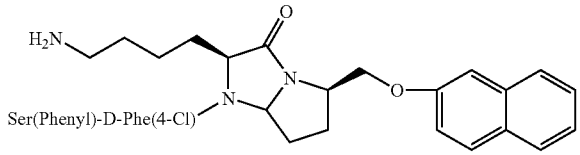

was synthesized by the general method of scheme 1 as set forth in Example 1. The molecular weight was determined to be 712.2 ESI-MS(M+1) by the method of Example 9. Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 72% | 20% | 56% | 52% |

EXAMPLE 51

A compound of the following structure:

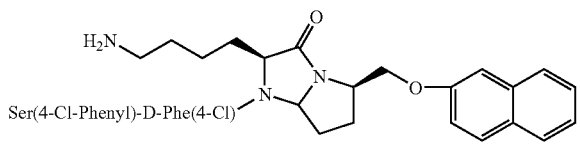

was synthesized by the general method of scheme 1 as set forth in Example 1. The molecular weight was determined to be 746.2 ESI-MS(M+1) by the method of Example 9. Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 52% | 28% | 37% | 40% |

EXAMPLE 52

A compound of the following structure:

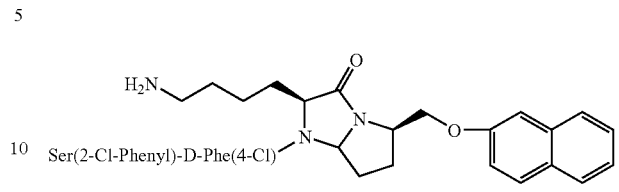

was synthesized by the general method of scheme 1 as set forth in Example 1. The molecular weight was determined to be 746.2 ESI-MS(M+1) by the method of Example 9. Competitive inhibition testing of the compound against $^{125}$I-NDP-α-MSH following the methods of Example 3 yielded the following results (average of triplicates with actual mean values described):

| Inhibition at 1 μM | | | |
|---|---|---|---|
| MC1-R | MC3-R | MC4-R | MC5-R |
| 42% | 15% | 37% | 22% |

EXAMPLE 53

A compound of the following structure:

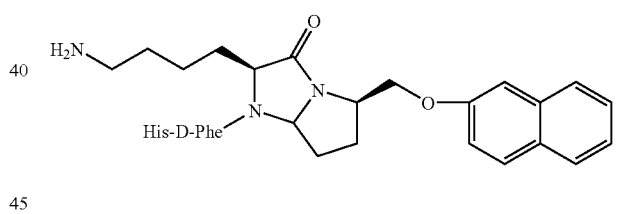

was synthesized by the general method of scheme 1 as set forth in Example 1. The molecular weight was determined to be 638.4 ESI-MS(M+1) by the method of Example 9. Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 94% | 9% | 10% | 0% |

In a cAMP assay as in Example 5 for determination of agonist/antagonist status, it was determined that the compound was an agonist as to MC1-R. The Ki was determined by the method of Example 4, with the following results:

| Ki (nM) | | | |
|---|---|---|---|
| MC1-R | MC3-R | MC4-R | MC5-R |
| 8 | >1 µM | >1 µM | >1 µM |

EXAMPLE 54

5-,5-membered bicyclic ring core compounds were synthesized by the general method of scheme 1 as set forth in Example 1. Mass analysis was conducted by the method of Example 9, and competitive inhibition testing of the compound against $^{125}$I-NDP-α-MSH followed the methods of Example 3. The compounds of this example have the following general formula, with variable assignments as given in Table 1:

TABLE 1

| | R₁ | R₃ | % Inhibition at 1 µM at Receptor for: | | | | |
|---|---|---|---|---|---|---|---|
| | | | MC1 | MC3 | MC4 | MC5 | Mass |
| A | naphthalen-2-yloxyethyl | 4-chloro-phenyl (α-amino ketone) | 92 | 66 | 92 | 63 | 563.7 |
| B | naphthalen-2-yloxyethyl | 2,4-dichloro-phenyl (α-amino ketone) | 54 | 75 | 98 | 69 | 597.8 |
| C | naphthalen-2-yloxyethyl | 2,4-difluoro-phenyl (α-amino ketone) | 48 | 16 | 43 | 10 | 565.9 |
| D | naphthalen-2-ylethyl | 4-chloro-phenyl (α-amino ketone) | 94 | 55 | 83 | 39 | 547.4 |
| E | naphthalen-2-ylethyl | 3-chloro-phenyl (α-amino ketone) | 82 | 31 | 68 | 24 | 547.5 |

TABLE 1-continued
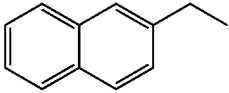
|   | R₁ | R₃ | MC1 | MC3 | MC4 | MC5 | Mass |
|---|---|---|---|---|---|---|---|
| F | 2-naphthylethyl | 2-Cl-Phe | 61 | 20 | 68 | 7 | 547.5 |
| G | 2-naphthylethyl | 2,4-diCl-Phe | 76 | 63 | 93 | 46 | 581.3 |
| H | 2-naphthylethyl | 3,4-diCl-Phe | 76 | 48 | 81 | 39 | 581.4 |
| I | 2-naphthylethyl | 4-CF₃-Phe | 49 | 31 | 72 | 29 | 581.5 |
| J | 2-naphthylethyl | 4-CH₃-Phe | 91 | 41 | 70 | 28 | 527.5 |
| K | 2-naphthylethyl | Phe | 81 | 11 | 42 | 15 | 513.5 |
| L | 2-naphthylethyl | 4-CN-Phe | 48 | 12 | 28 | 15 | 537.9 |
% Inhibition at 1 μM at Receptor for:

TABLE 1-continued

| | R₁ | R₃ | MC1 | MC3 | MC4 | MC5 | Mass |
|---|---|---|---|---|---|---|---|
| M | naphthyl-ethyl | MeO-phenyl-CH₂-CH(NH₂)-C(O)- | 71 | 30 | 49 | 34 | 543.0 |
| N | naphthyl-ethyl | 4-Cl-phenyl-pyrrolidine-C(O)- | 61 | 27 | 63 | 54 | 572.9 |
| O | naphthyl-O-CH₂- | 2,4-diCl-phenyl-CH₂-CH(NH₂)-CH₂CH₃ | 2 | 28 | 91 | 49 | 582.8 |
| P | naphthyl-O-CH₂- (S) | 2,4-diCl-phenyl-CH₂-CH(NH₂)-C(O)- | 11 | 6 | 20 | 8 | 597.0 |
| Q | naphthyl-O-CH₂- (S) | 4-Cl-phenyl-CH₂-CH(NH₂)-C(O)- | 9 | 4 | 12 | 7 | 563.0 |

In a functional assay as in Example 5, compound B above was an agonist at MC1-R, MC4-R and MC5-R. The Ki was determined by the method of Example 4 for compound B, with the following results:

| Ki (nM) for Compound B | | | |
|---|---|---|---|
| MC1-R | MC3-R | MC4-R | MC5-R |
| 144 | 132 | 11 | 499 |

In a functional assay as in Example 5, compound G above was an agonist at MC4-R and MC5-R. The Ki was determined by the method of Example 4 for compound G, with the following results:

| Ki (nM) for Compound G | | | |
|---|---|---|---|
| MC1-R | MC3-R | MC4-R | MC5-R |
| 63 | 121 | 19 | 1050 |

The Ki was determined by the method of Example 4 for compound O, with the following results:

| Ki (nM) for Compound O | | | |
|---|---|---|---|
| MC1-R | MC3-R | MC4-R | MC5-R |
| 848 | 505 | 29 | 689 |

EXAMPLE 55

A 6-,5-membered bicyclic ring core compound was synthesized by the following method. To a solution of N-(tert-butoxycarbonyl)-O-benzyl-hydroxyproline in DCM, NMM (1 eq) and iso-butyl chloroformate (1 eq) were added at −15° C. and stirred for 30 minutes. A solution of N,O-dimethylhydroxylamine hydrochloride (1.5 eq) and NMM (1.5 eq) was added to the mixture, and after 30 minutes the mixture was allowed to attain room temperature and stirred overnight. Solvent was evaporated and residue purified on a silica gel column using an ethyl acetate-hexane mixture (v/v=2/1) to yield N-(tert-butoxycarbonyl)-O-benzyl-hydroxyproline dimethyihydroxamide. The O-benzyl group was removed using palladium (10%) on carbon in methanol under hydrogen (1 atm.) for 10 hours. After filtration, the solvent was evaporated and the resulting compound was used for next step reaction after drying under vacuum. The formation of an ether bond was accomplished by either of the following Method A or Method B.

Method A. N-(tert-butoxycarbonyl)-hydroxyproline N,O-dimethylhydroxamide, aromatic alcohol (1.5 eq) and TPP were dissolved in THF. To this solution DEAD (1.5 eq) in THF was added dropwise at 0° C. After 12 hours, the solvent was evaporated, the residue taken in ethyl acetate and washed successively with 1 N sodium hydroxide, water and brine followed by drying over sodium sulfate. Silica gel column chromatography using ethyl acetate and hexane (v/v=2/1) yielded purified O-substituted N-(tert-butoxycarbonyl)-hydroxyproline N,O-dimethylhydroxamide.

Method B. Methanesulfonyl chloride (2 eq) was slowly added at 0° C. to a DCM solution of N-(tert-butoxycarbonyl)-hydroxyproline N,O-dimethylhydroxamide and TEA (2 eq). The reaction mixture was stirred for an additional 10 minutes and allowed to attain room temperature with continued stirring for an additional 45 minutes. The solvent was then evaporated and residue taken in water. It was extracted with ethyl acetate (twice) and the combined organic layer was washed with brine and dried over sodium sulfate. The solvent was evaporated and residue dried under vacuum to give O-mesyl N-(tert-butoxycarbonyl)-hydroxyproline N,O-dimethylhydroxamide. The yield from this reaction.

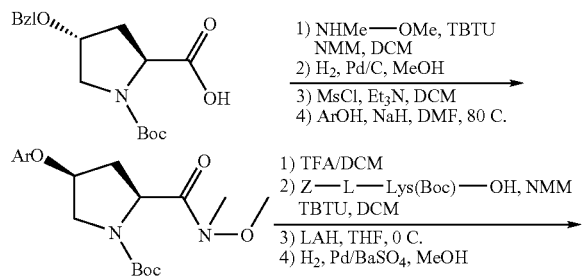

Schem 4

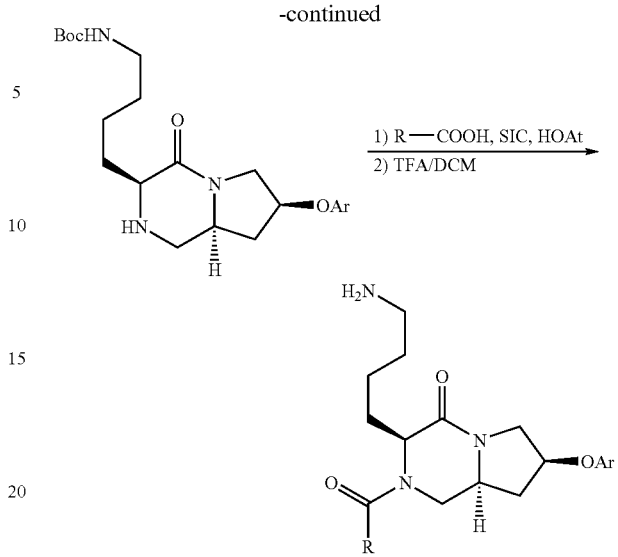

approached 100%. To a suspension of sodium hydride (2 eq) in DMF was added an aromatic alcohol (2 eq) taken in DMF under vigorous stirring. After completion of the hydrogen release, the solution was added to the DMF solution of O-mesyl N-(tert-butoxycarbonyl)-hydroxyproline N,O-dimethylhydroxamide and stirred for 16 hours. The reaction temperature then was raised to 90° C. with continued stirring for 24-48 hours. After cooling, the reaction mixture was poured into water and extracted twice with ethyl acetate. The combined organic layer was washed with water (twice), brine (once), and dried over sodium sulfate. The solvent was evaporated and product purified as described in Example 55, Method A.

Following addition of the ether bond using the above methods, the tert-butoxycarbonyl group from O-substituted N-(tert-butoxycarbonyl)-hydroxyproline N,O-dimethylhydroxamide was removed by treatment with TFA (25%) in DCM for 1 hour. After evaporating the solvent, the compound was dissolved in DCM and NMM (1 eq) added. The compound was mixed with a reaction mixture obtained separately by slowly mixing isobutyl chloroformate at −15° C. for 30 minutes with a DCM solution of Z-Lys(Boc)—OH (1 eq) and NMM (1 eq). The combined solution was then stirred at room temperature for an additional 16 hours. After evaporating the solvent, the residue was purified on a silica gel column with ethyl acetate as an eluant.

O-substituted N-(N-benzyloxycarbonyl-N'-tert-butoxycarbonyl-lysyl)-hydroxyproline N,O-dimethylhydroxamide obtained above was dissolved in dry THF and the solution cooled to 0° C. LAH (1.25 eq) in THF was slowly added and the reaction mixture stirred for an additional 30 minutes. The reaction was quenched with aqueous potassium hydrogen sulfate (1.75 eq). The solution was diluted with ether and washed with 1 N hydrogen chloride, saturated sodium hydrogen carbonate, and brine. The organic layer was dried over sodium sulfate and solvent evaporated to dryness. The resulting aldehyde derivative was used without purification in the next reaction.

The product from the preceding step was dissolved in methanol and a catalytic amount of palladium (5%) in barium sulfate was added and the mixture hydrogenated at 1 atm. of hydrogen gas for 3 days. The reaction was monitored by mass analysis. The resulting mixture was filtered and the solvent evaporated to give 2,7-disubstituted hexahydro-pyrrolo[1,2-a]pyrazin-4-one. This compound was used further without purification.

The 2,7-disubstituted hexahydro-pyrrolo[1,2-a]pyrazin-4-one was coupled with desired amino acid residues (2 eq) using HOAt (2 eq) and DIC (2 eq) in DMF overnight at room temperature. Other amino acids derivatives were coupled in a similar fashion. The final fully protected compound was purified by flash chromatography (ethyl acetate/hexane, v/v=½). In appropriate instances, the Fmoc group was removed by treatment with diethyl amine (20%) in ethyl acetate while Boc groups were removed by treatment with TFA (30%) in DCM for 1 hour. The final compounds were obtained in pure form after their purification by HPLC.

The compound had the following structure:

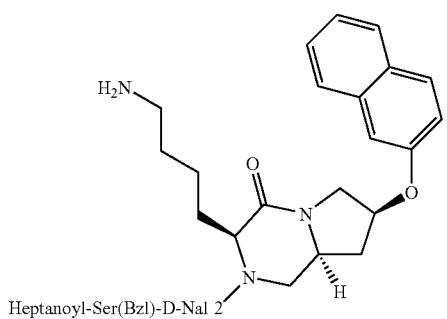

Heptanoyl-Ser(Bzl)-D-Nal 2

The molecular weight was determined to be 840.4 ESI-MS(M+1) by the method of Example 9. Competitive inhibition testing of the compound against $^{125}$I-NDP-α-MSH following the methods of Example 3 yielded the following results (average of triplicates with actual mean values described; experimental results less than 0% reported as 0%):

| Inhibition at 1 μM | | | |
|---|---|---|---|
| MC1-R | MC3-R | MC4-R | MC5-R |
| 33% | 0% | 0% | 0% |

EXAMPLE 56

A 6-,5-membered bicyclic ring core compounds was synthesized by the method employed for the synthesis of the compound of Example 55. The compound had the following structure:

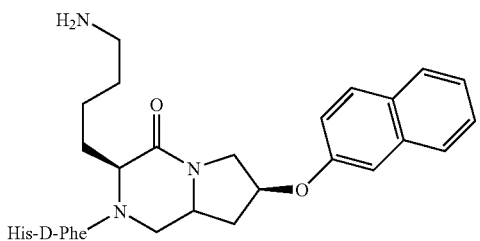

His-D-Phe

The molecular weight was determined to be 638.4 ESI-MS(M+1) by the method of Example 9. The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound having the structure:

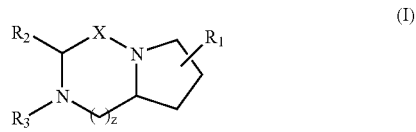

(I)

or a stereoisomer or pharmaceutically acceptable salt thereof, wherein $R_1$ is $-L_1-J$;

$R_2$ is $(CH_2)_y-W$;

$R_3$ is $-L_2-Q$;

$L_1$ is a linker selected from the group consisting of $-(CH_2)_y-$, $-O-(CH_2)_y-$, $-O-$, $-NH-(CH_2)_y-$, $-(C=O)(CH_2)_y-$, $-(C=O)-O-(CH_2)_y-$ and $-CH_2(C=O)NH-$;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or $-O-$, and substituted or unsubstituted aromatic fused heterobicyclic ring groups; wherein in each instance the rings comprise 5 or 6 ring atoms;

W is a heteroatom unit with at least one cationic center, hydrogen bond donor or hydrogen bond acceptor wherein at least one atom is N;

$L_2$ is a linker selected from the group consisting of

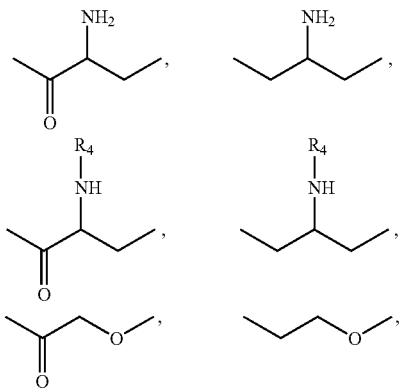

-continued

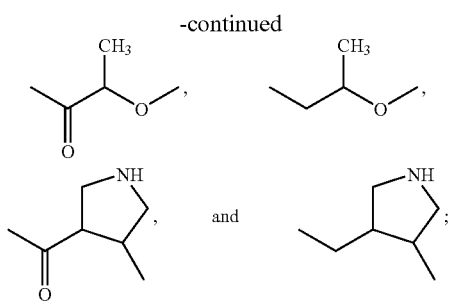

Q is an aromatic carbocyclic ring selected from the group consisting of phenyl, substituted phenyl, naphthyl and substituted naphthyl;

$R_4$ is a unit selected from the group consisting of an amine capping group, an amino acid residue, and an amino acid residue with an amine capping group;

X is C=O;

z is 0; and y is at each occurrence independently from 1 to 6.

2. The compound of claim 1 wherein J is a substituted or unsubstituted ring structure selected from the group consisting of

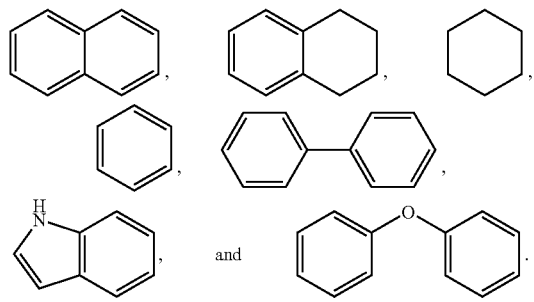

3. The compound of claim 1 wherein at least one ring comprising J is functionalized with one or more halogen, alkyl or aryl groups.

4. The compound of claim 1 wherein $R_1$ is selected from the group consisting of

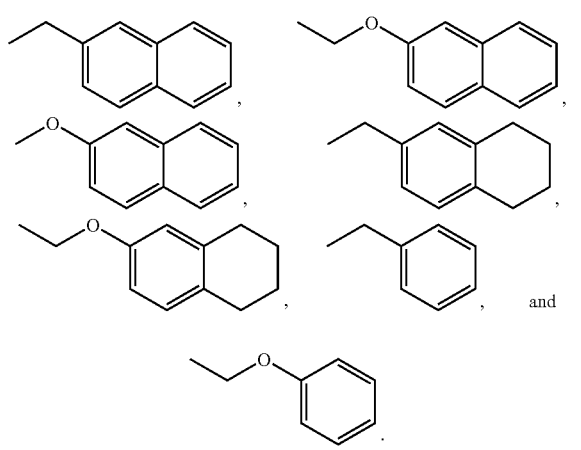

5. The compound of claim 1 wherein $R_1$ is selected from the group consisting of

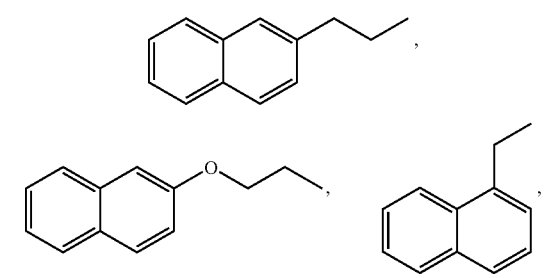

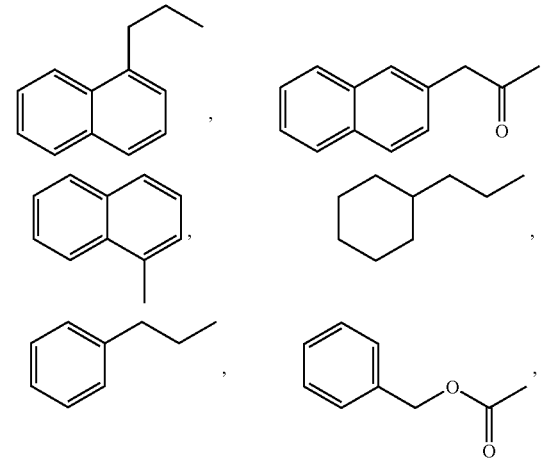

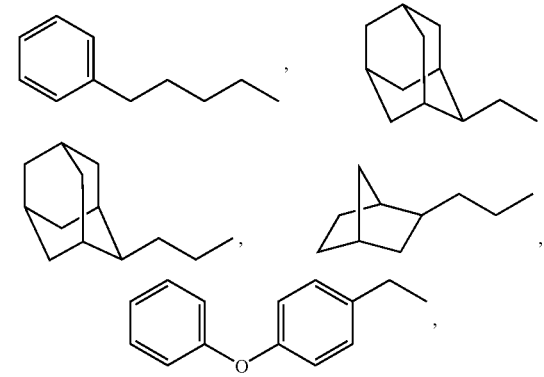

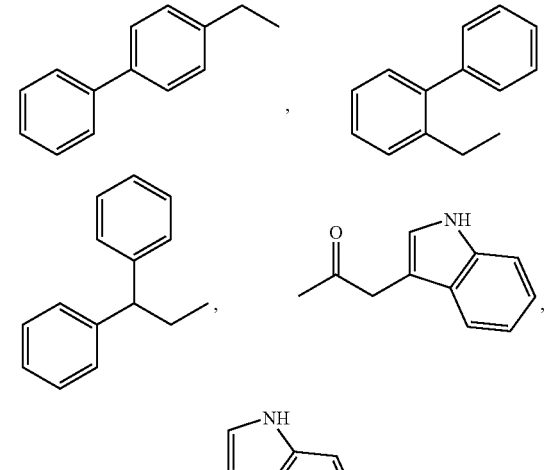

-continued

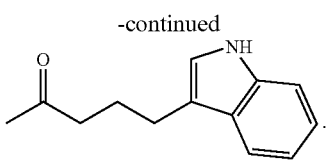

6. The compound of claim 1 wherein W comprises a cationic center selected from the group consisting of NH₂ and NH(C=NH)NH₂.

7. The compound of claim 1 wherein W is selected from the group consisting of —NHCOCH₃, —CONHCH₃, —NH(C=NH)NHMe, —NH(C=NH)NHEt, —NH(C=NH)NHPr, —NH(C=NH)NHPr—I, —NH(C=NH)NH₂,

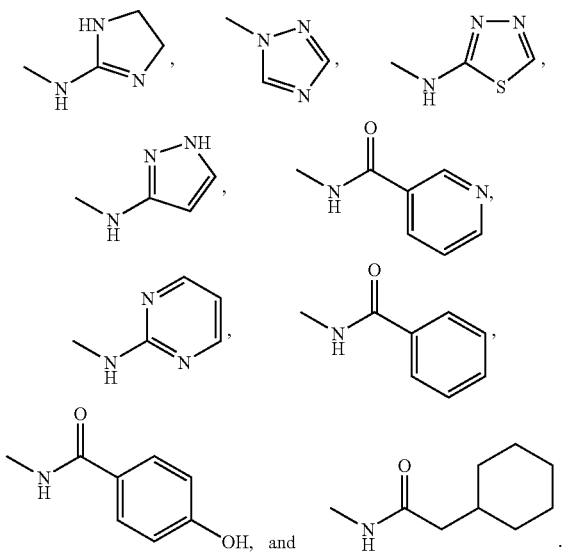

8. The compound of claim 1 wherein R₂ is selected from the group consisting of

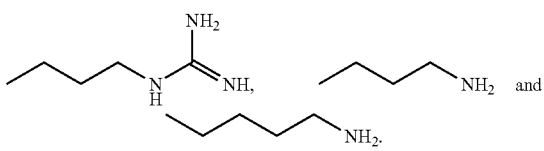

9. The compound of claim 1 where Q is

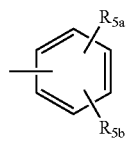

and wherein $R_{5a}$ and $R_{5b}$ are optional ring substituents, and when one or both are present, are the same or different and independently hydroxyl, halogen, alkyl, or aryl groups attached directly or through an ether linkage.

10. The compound of claim 9 wherein the alkyl group is —CH₃ or —OCH₃.

11. The compound of claim 1 wherein R₄ is an amine capping group selected from the groups consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc, and 8-Aoc.

12. The compound of claim 1 wherein R₃ is a D-amino acid including an aromatic carbocyclic ring selected from the group consisting of phenyl, substituted phenyl, naphthyl and substituted naphthyl.

13. The compound of claim 1 wherein R₃ is a D-amino acid with an amine capping group and an aromatic carbocyclic ring selected from the group consisting of phenyl, substituted phenyl, naphthyl and substituted naphthyl.

14. The compound of claim 1 wherein R₃ is a dipeptide consisting of a D-amino acid including an aromatic carbocyclic ring selected from the group consisting of phenyl, substituted phenyl, naphthyl and substituted naphthyl and a second amino acid residue, wherein the D-amino acid is bonded to the ring nitrogen.

15. The compound of claim 1 wherein R₃ is a dipeptide consisting of a D-amino acid including an aromatic carbocyclic ring selected from the group consisting of phenyl, substituted phenyl, naphthyl and substituted naphthyl and a second amino acid residue with an amine capping group.

16. The compound of claim 1 wherein R₃ comprises a D-amino acid selected from the group consisting of Phe, Phe(2-Cl), Phe(4-Cl), Phe(2,4-diCl), Phe(2,4-diF), Phe(3,4-diCl), Phe(4-NO₂), Phe(4-Me), Phe(4-Phenyl), HPhe, pF-Phe, Phe(4-Br), Phe(4-CF₃), Phe(3,4-diF), Phe(4-I),Phe(4-Me), Phe(2-Me, 4-Cl), Phe(2-F, 4-Cl), Phe(2,4-diMe), Phe(2-Cl4-CF₃), and Phe(3,4-di-OMe).

17. The compound of claim 1 wherein R₃ comprises a D-amino acid selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys(Z-2'Br), Lys(Bz), Thr(Bzl), Cys(Bzl), (N-PhEt)Nal2, Phg, 3-Pya, Qal(2'), Sal, Tpi, Tyr(2,6-DiCl-Bzl) and Tyr(Bzl).

18. The compound of claim 1 wherein R₃ comprises a second amino acid residue that is a an L-amino acid selected from the group consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp (Bzl), Cha, Chg, Cmpi, Disc, Dpr(beta-Ala), GM, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) and Thr(O-2-Cl-Phenyl), Nle, Leu, lie, Val and Beta-Ala.

19. The compound of claim 1 wherein R₃ comprises an amine capping group selected from the group consisting of hexyl, hexanoyl, heptanoyl, acetyl, phenylacetyl, cyclohexylacetyl, naphthylacetyl, cinnamoyl, benzyl, benzoyl, 7'-amino heptanoyl, 12-Ado, 6-Ahx, Amc, and 8-Aoc.

20. A compound having the structure:

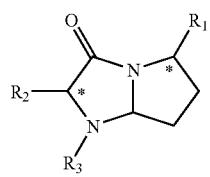

or a stereoisomer or pharmaceutically acceptable salt thereof,
wherein
$R_1$ is $-L_1-J$;
$R_2$ is $(CH_2)_y-W$;
$R_3$ is $-L_2-Q$;
$L_1$ is a linker selected from the group consisting of $-(CH_2)_y-$, $-O-(CH_2)_y-$, $-O-$, $-NH-(CH_2)_y-$, $-(C=O)(CH_2)_y-$, $-(C=O)-O-(CH_2)_y-$, and $-CH_2(C=O)NH-$;
J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or $-O-$, and substituted or unsubstituted aromatic fused heterobicyclic ring groups; wherein in each instance the rings comprise 5 or 6 ring atoms;
W is a heteroatom unit with at least one cationic center, hydrogen bond donor or hydrogen bond acceptor wherein at least one atom is N;
$L_2$ is a linker selected from the group consisting of

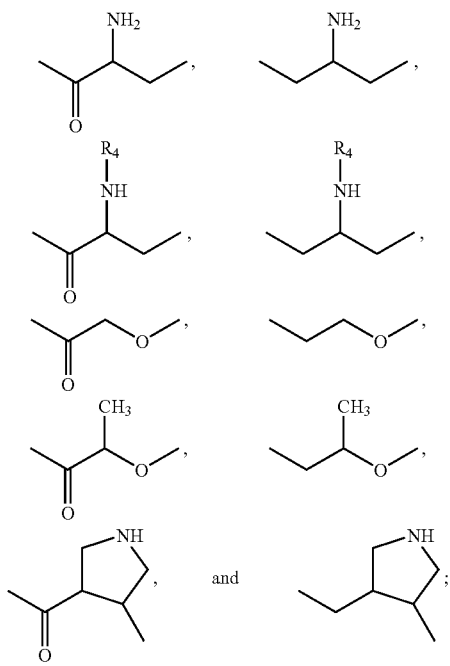

Q is an aromatic carbocyclic ring selected from the group consisting of phenyl, substituted phenyl, naphthyl and substituted naphthyl;

$R_4$ is a unit selected from the group consisting of an amine capping group, an amino acid residue, and an amino acid residue with an amine capping group; and
y is at each occurrence independently from 1 to 6;
wherein the carbon atoms marked with an asterisk can have any stereochemical configuration.

21. The compound of claim 20 wherein J is a substituted or unsubstituted ring structure selected from the group consisting of

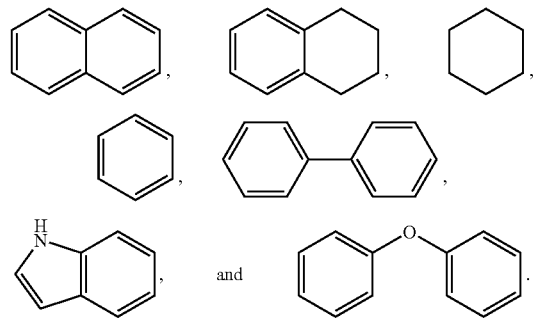

22. The compound of claim 20 wherein at least one ring comprising J is functionalized with one or more halogen, alkyl or aryl groups.

23. The compound of claim 20 wherein $R_1$ is selected from the group consisting of

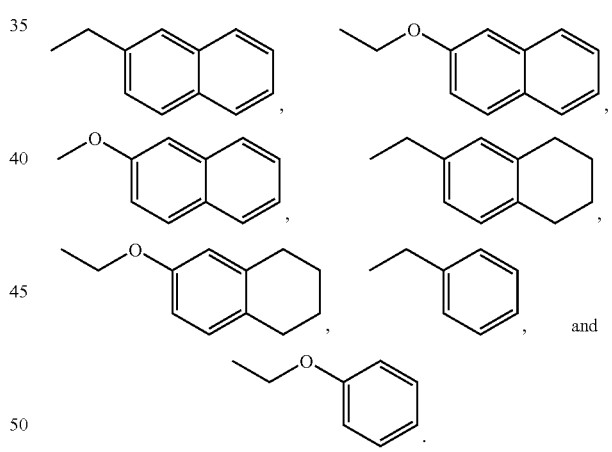

24. The compound of claim 20 wherein $R_1$ is selected from the group consisting of

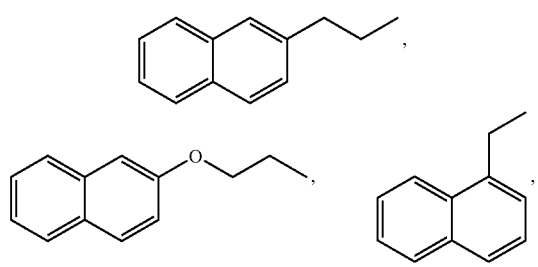

-continued

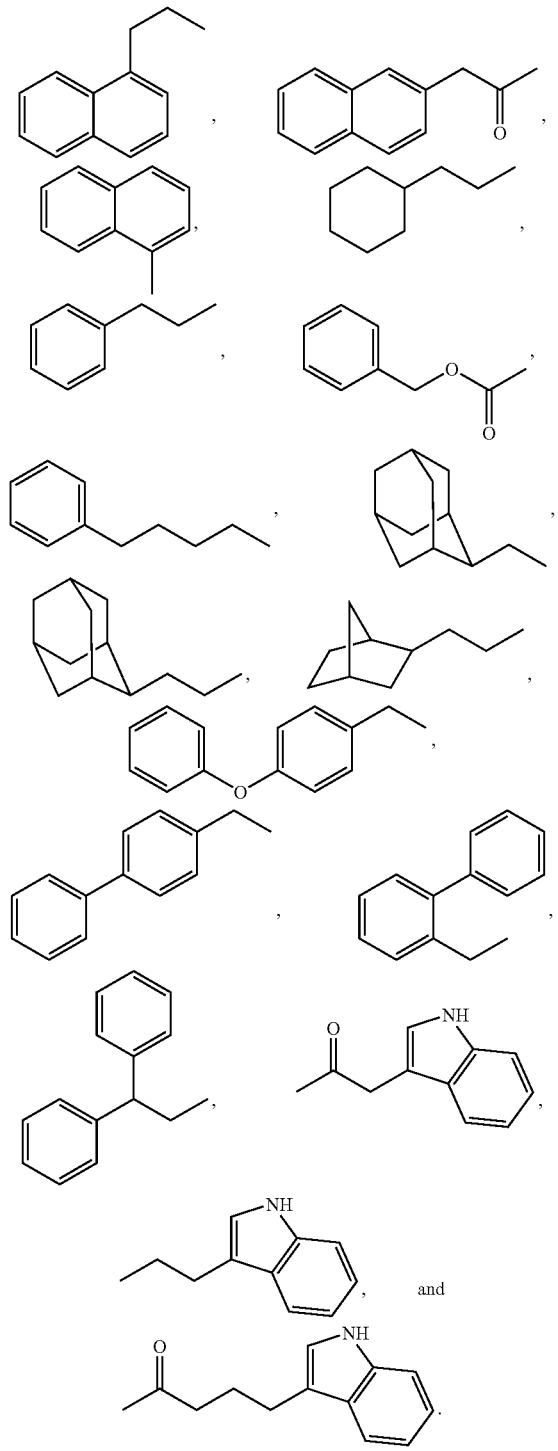

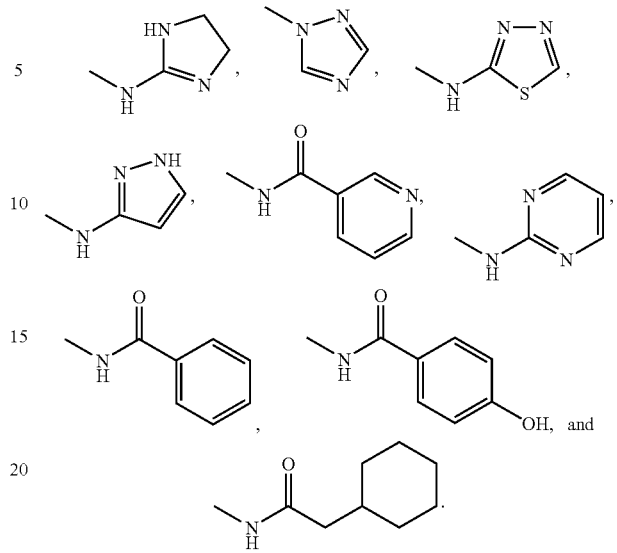

25. The compound of claim 20 wherein W comprises a cationic center selected from the group consisting of $NH_2$ and $NH(C=NH)NH_2$.

26. The compound of claim 20 wherein W is selected from the group consisting of —NHCOCH$_3$, —CONHCH$_3$, —NH(C=NH)NHMe, —NH(C=NH)NHEt, —NH(C=NH)NHPr, —NH(C=NH)NHPr—I, —NH(C=NH)NH$_2$, 27. The compound of claim 20 wherein $R_2$ is selected from the group consisting of

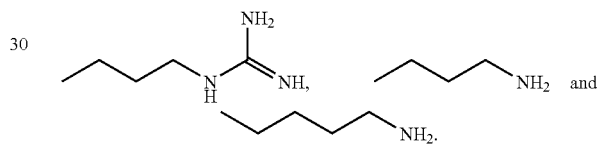

28. The compound of claim 20 where Q is

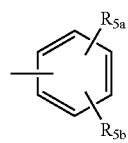

and wherein $R_{5a}$ and $R_{5b}$ are optional ring substituents, and when one or both are present, are the same or different and independently hydroxyl, halogen, alkyl, or aryl groups attached directly or through an ether linkage.

29. The compound of claim 28 wherein the alkyl group is —CH$_3$ or —OCH$_3$.

30. The compound of claim 20 wherein $R_4$ is an amine capping group selected from the groups consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc, and 8-Aoc.

31. The compound of claim 20 wherein $R_3$ is a D-amino acid including an aromatic carbocyclic ring selected from the group consisting of phenyl, substituted phenyl, naphthyl and substituted naphthyl.

32. The compound of claim 20 wherein $R_3$ is a D-amino acid with an amine capping group and an aromatic carbocyclic ring selected from the group consisting of phenyl, substituted phenyl, naphthyl and substituted naphthyl.

33. The compound of claim 20 wherein $R_3$ is a dipeptide consisting of a D-amino acid including an aromatic carbocyclic ring selected from the group consisting of phenyl, substituted phenyl, naphthyl and substituted naphthyl and a second amino acid residue, wherein the D-amino acid is bonded to the ring nitrogen.

34. The compound of claim 20 wherein $R_3$ is a dipeptide consisting of a D-amino acid including an aromatic carbocyclic ring selected from the group consisting of phenyl, substituted phenyl, naphthyl and substituted naphthyl and a second amino acid residue with an amine capping group.

35. The compound of claim 20 wherein $R_3$ comprises a D-amino acid selected from the group consisting of Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl,4-CF$_3$), and Phe(3,4-di-OMe).

36. The compound of claim 20 wherein $R_3$ comprises a D-amino acid selected from the group consisting of Pgl, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Ser(p-Cl-Phenyl), Lys(Z), Lys(Z-2'Br), Lys(Bz), Thr(Bzl), Cys(Bzl), (N-PhEt)Nal2, Phg, 3-Pya, Qal(2'), Sal, Tpi, Tyr(2,6-DiCl-Bzl) and Tyr(Bzl).

37. The compound of claim 20 wherein $R_3$ comprises a second amino acid residue that is a an L-amino acid selected from the group consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp (Bzl), Cha, Chg, Cmpi, Disc, Dpr(beta-Ala), GM, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

38. The compound of claim 20 wherein $R_3$ comprises an amine capping group selected from the group consisting of hexyl, hexanoyl, heptanoyl, acetyl, phenylacetyl, cyclohexylacetyl, naphthylacetyl, cinnamoyl, benzyl, benzoyl, 7'-amino heptanoyl, 12-Ado, 6-Ahx, Amc, and 8-Aoc.

39. A compound having the structure:

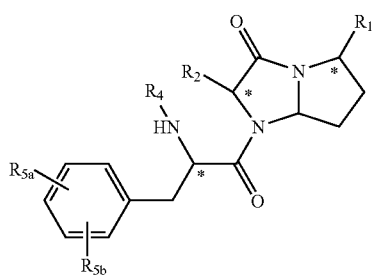

(III)

or a stereoisomer or pharmaceutically acceptable salt thereof,
wherein
$R_1$ is -$L_1$-J;
$R_2$ is $(CH_2)_y$—W;
$R_4$ is H or a unit selected from the group consisting of an amine capping group, a second amino acid residue, and a second amino acid residue with an amine capping group;

$R_{5a}$ and $R_{5b}$ are optional ring substituents, and when one or both are present, are the same or different and independently hydroxyl, halogen, alkyl, or aryl groups attached directly or through an ether linkage;

$L_1$ is a linker selected from the group consisting of —$(CH_2)_y$—, —O—$(CH_2)_y$—, —O—, —NH—$(CH_2)_y$—, —(C=O)$(CH_2)_y$—, —(C=O)—O—$(CH_2)_y$—, and —$CH_2$(C=O)NH—;

J is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, substituted or unsubstituted aromatic carbocyclic ring groups wherein the rings are joined by a bond or —O—, and substituted or unsubstituted aromatic fused heterobicyclic ring groups; wherein in each instance the rings comprise 5 or 6 ring atoms;

W is a heteroatom unit with at least one cationic center, hydrogen bond donor or hydrogen bond acceptor wherein at least one atom is N; and y is at each occurrence independently from 1 to 6;

wherein the carbon atoms marked with an asterisk can have any stereochemical configuration.

40. The compound of claim 39 wherein J is a substituted or unsubstituted ring structure selected from the group consisting of

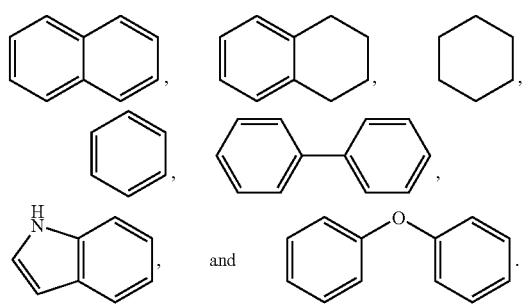

41. The compound of claim 39 wherein at least one ring comprising J is functionalized with one or more halogen, alkyl or aryl groups.

42. The compound of claim 39 wherein $R_1$ is selected from the group consisting of

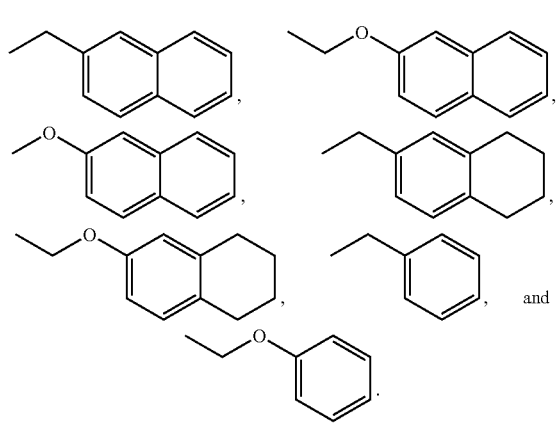

43. The compound of claim 39 wherein $R_1$ is selected from the group consisting of

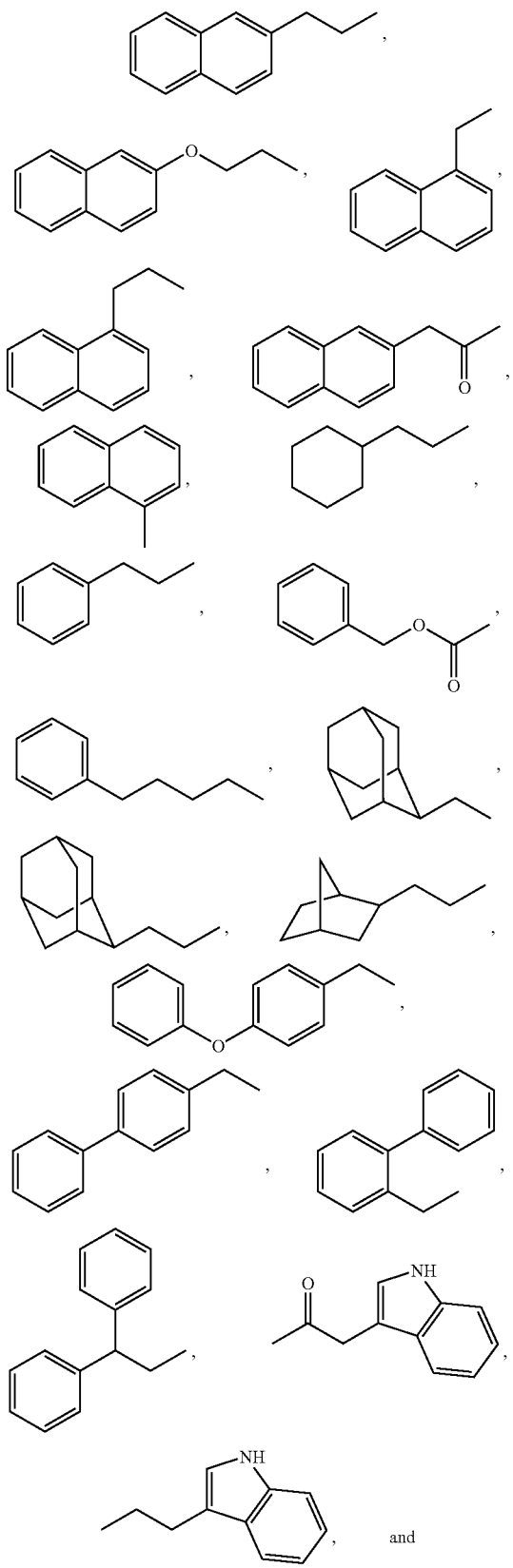

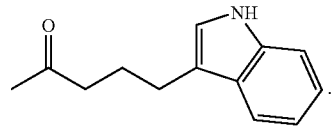

44. The compound of claim 39 wherein W comprises a cationic center selected from the group consisting of $NH_2$ and $NH(C=NH)NH_2$.

45. The compound of claim 39 wherein W is selected from the group consisting of —$NHCOCH_3$, —$CONHCH_3$, —$NH(C=NH)NHMe$, —$NH(C=NH)NHEt$, —$NH(C=NH)NHPr$, —$NH(C=NH)NHPr$—I, —$NH(C=NH)NH_2$,

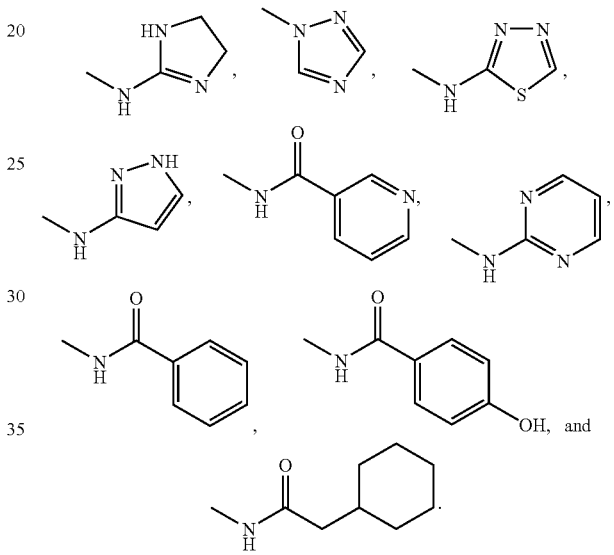

46. The compound of claim 39 wherein $R_2$ is selected from the group consisting of

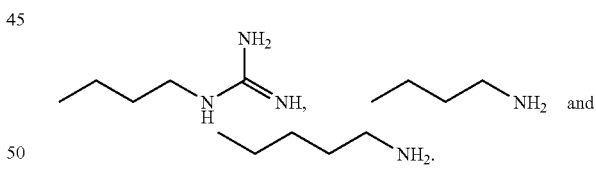

47. The compound of claim 39 wherein $R_4$ comprises an amine capping group selected from the groups consisting of hexyl, hexanoyl, heptanoyl, acetyl, phenylacetyl, cyclohexylacetyl, naphthylacetyl, cinnamoyl, benzyl, benzoyl, cinnamoyl, 12-Ado, 7'-amino heptanoyl, 6-Ahx, Amc, and 8-Aoc.

48. The compound of claim 39 wherein $R_4$ comprises a second amino acid residue that is a an L-amino acid selected from the group consisting of Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp (Bzl), Cha, Chg, Cmpi, Disc, Dpr(beta-Ala), GM, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer (Bzl), Ser(O-2-Naphthyl), Ser(O-Phenyl), Ser(O-4-Cl-Phenyl), Ser(O-2-Cl-Phenyl), Thr(Bzl), Tic, Beta-homoThr (Bzl), Thr(O-2-Naphthyl), Thr(O-Phenyl), Thr(O-4-Cl-Phenyl) and Thr(O-2-Cl-Phenyl), Nle, Leu, Ile, Val and Beta-Ala.

49. A composition comprising a compound of any one of claims 1, 20 and 39 in combination with a pharmaceutically acceptable carrier.

50. A method for altering a disorder or condition associated with the activity of a melanocortin receptor, comprising administering to a patient a therapeutically effective amount of the composition of claim 49.

51. The method of claim 50 wherein the disorder or condition is an eating disorder.

52. The method of claim 51 wherein the eating disorder is cachexia.

53. The method of claim 51 wherein the eating disorder is obesity and associated impairment of energy homeostasis.

54. The method of claim 50 wherein the disorder or condition is sexual dysfunction.

55. The method of claim 54 wherein the sexual dysfunction is erectile dysfunction.

56. The method of claim 54 wherein the sexual dysfunction is female sexual dysfunction.

* * * * *